(12) United States Patent
Hunter et al.

(10) Patent No.: US 6,251,657 B1
(45) Date of Patent: Jun. 26, 2001

(54) ANAEROBIC BIODEGRADATION OF UNSATURATED, SATURATED, AROMATIC AND HALOGENATED HYDROCARBONS

(75) Inventors: Robert M. Hunter; Frank M. Stewart; Tamara Darsow; Macgregor L. Fogelsong, all of Gallatin, MT (US)

(73) Assignee: YES Technologies, Kamuela, HI (US)

( * ) Notice: Subject to any disclaimer, the term of this patent is extended or adjusted under 35 U.S.C. 154(b) by 0 days.

(21) Appl. No.: 09/312,014

(22) Filed: May 14, 1999

Related U.S. Application Data

(60) Division of application No. 08/545,498, filed on Oct. 19, 1995, now Pat. No. 5,942,117, which is a continuation-in-part of application No. 08/247,070, filed on May 20, 1994, which is a continuation-in-part of application No. 07/940,439, filed on Sep. 4, 1992, now Pat. No. 5,342,769, which is a continuation-in-part of application No. 07/926,047, filed on Aug. 4, 1992, now Pat. No. 5,922,204.

(51) Int. Cl.$^7$ ........................................ C12N 1/12
(52) U.S. Cl. ...................... 435/264; 435/248; 435/252.1; 435/253.3
(58) Field of Search .................................. 435/264, 248, 435/252.1, 253.3

(56) References Cited

U.S. PATENT DOCUMENTS 5,942,117 * 8/1999 Hunter et al. .................... 210/610

* cited by examiner

Primary Examiner—Leon B. Lankford, Jr.
(74) Attorney, Agent, or Firm—Robert M. Hunter

(57) ABSTRACT

An apparatus and method for anaerobic biodegradation, bioremediation or bioprocessing of hydrocarbons dissolved in an aqueous matrix, such as wastewater, groundwater, or slurry. Dissolved alkanes (saturated hydrocarbons), alkenes (unsaturated hydrocarbons), aromatic hydrocarbons and/or halogenated hydrocarbons are metabolized or cometabolized. In one form, the invention involves introducing an aqueous stream comprising at least one dissolved aromatic hydrocarbon (such as benzene, toluene, ethylbenzene, o-xylene, m-xylene, p-xylene, phenol, o-cresol, m-cresol, or p-cresol) and a dissolved oxide of nitrogen [such as nitrate ($NO_3^-$), nitrite ($NO_2^-$), nitric oxide (NO) and nitrous oxide ($N_2O$)] to a reactor, and operating said reactor under conditions that support denitrification of the aromatic hydrocarbon. Alternatively, the aqueous stream may comprise at least one alkane (such as ethane) and/or at least one alkene (such as ethene or ethylene) and biodegradation of these compounds is accomplished. In a preferred form, the aqueous stream also comprises at least one dissolved halogenated hydrocarbon (such as tetrachloroethylene, trichloroethylene, or 1,1,1-trichloroethane) and dehalogenation of the halogenated hydrocarbon is accomplished. The reactor may be a continuous stirred tank reactor, a batch (or sequencing batch) reactor, a plug-flow reactor, a fixed-film reactor, or a pore space in an underground aquifer in situ. The reactor is operated in such a way that molecular oxygen is excluded from the space or zone in which the biodegradation is occurring and the other requirements of denitrifying bacteria are met. In some implementations, kinetic control (control of mean cell residence time) is used to enrich a denitrifying culture in the reactor.

7 Claims, 10 Drawing Sheets

ANAEROBIC BIODEGRADATION OF UNSATURATED, SATURATED, AROMATIC AND HALOGENATED HYDROCARBONS

CROSS-REFERENCES TO RELATED APPLICATIONS

This application is a division of application Ser. No. 08/545,498, filed Oct. 19, 1995, (now U.S. Pat. No. 5,942,117 which application is incorporated by reference herein as if fully set forth. The present application is a continuation in part of copending application Ser. No. 08/247,070 filed May 20, 1994, entitled "Apparatus for Microbial Dehalogenation," which is a continuation in part of application Ser. No. 07/940,439 filed Sep. 4, 1992, entitled "Microbial Dehalogenation Using Methanosarcina," which is now U.S. Pat. No. 5,342,769, which is a continuation in part of application Ser. No. 07/926,047, filed Aug. 4, 1992, entitled "Method and Apparatus for Bioremediation of Mixed Hazardous Wastes," now U.S. Pat. No. 5,922,204, which applications and patent are incorporated by reference herein as if fully set forth.

STATEMENT AS TO RIGHTS IN INVENTIONS MADE UNDER FEDERALLY-SPONSORED RESEARCH AND DEVELOPMENT

This invention was made with Government support under Small Business Innovation Research Contract No. DAAH01-93-C-R287 awarded by the Advanced Research Projects Agency (ARPA), a component of the U.S. Department of Defense. The Government has certain rights in the invention.

BACKGROUND OF THE INVENTION

The background of the invention is set forth in two parts: the field of the invention and the description of related art.

1. Field of the Invention

This invention relates to an apparatus and method for bioremediation of groundwater or treatment of wastewater contaminated with dissolved hydrocarbons (such as dissolved alkanes and alkenes), aromatic hydrocarbons (particularly benzene, toluene, ethylbenzene and xylenes) and/or halogenated hydrocarbons (particularly tetrachloroethylene, trichloroethylene, and 1,1,1-trichloroethane). In particular, it relates to biodegradation of such compounds by denitrifying microorganisms.

2. Description of Related Art

The activities of the U.S. Department of Defense (DoD), the U.S. Department of Energy (DOE) and their contractors result in the generation of large amounts of hazardous wastes. Many of the constituents of concern are waterborne or have become waterborne as a result of leaks or spills. Among the most troublesome of these wastes are organic solvents. Even at low concentrations these constituents are often toxic, tend to be resistant to conventional treatment methods and are persistent in the environment.

Most productive research on new biotechnologies for hazardous waste remediation is conducted from a reactor engineering perspective. Grady explained this phenomenon as follows (Grady, C. P. L., Jr. *Biological detoxification of hazardous wastes: What do we know? What should we know?* In Y. C. Wu ed.), *Proceedings of the International Conference on Physiochemical and Biological Detoxification of Hazardous Wastes.* Lancaster, Pa.: Technomic, 1989, pp. 3–16.):

"Many of the major advances in pollution control technology have come from the application of reactor engineering to wastewater treatment systems. Reactor engineering is based on the premise that, if the kinetics of a reaction can be expressed mathematically, then it is possible to investigate the impact of reactor type and configuration on the extent of reaction through application of mathematical models that incorporate both transport and reaction terms."

The reactor engineering approach involves gathering the information required to mathematically model various process options. Reliance on process modeling offers a number of advantages. First, development of the model in the early stages of the project can facilitate design of the experimental apparatus and procedures. Second, a model provides a framework for understanding the microbiology of the system under study. Finally, a calibrated model is a valuable tool for investigating applications of the knowledge gained during the research for the resulting scale-up of this knowledge.

Recent research has revealed the promise of novel bioremediation schemes that rely in part or totally on anaerobic processes. These include metabolic processes (such as aerobic respiration, denitrification, sulfate reduction and/or methanogenesis) and/or cometabolic processes (such as reductive dechlorination), (Hunter et al. *Biomimetic Process for Hazardous Waste Remediation.* Phase I Final Technical Report prepared for Defense Advanced Research Projects Agency, YES Inc, 1992).

Biotransformation of some of the compounds of interest applicable to bioremediation process design have been found to occur under denitrifying conditions. Bakker disclosed that a mixed culture can degrade phenol, o-cresol, m-cresol and p-cresol under anaerobic conditions in the presence of nitrate as the terminal electron acceptor (Bakker, G. *Anaerobic degradation of aromatic compounds in the presence of nitrate, FEMS Microbiology Letters,* 1, 103–108, 1977). Pure cultures of three Gram-negative, slightly curved, monotrichously flagellated rods, including strain DSM 981, were capable of phenol decomposition under anaerobic conditions in the presence of nitrate. Pillis and Davis (in U.S. Pat. No. 4,352,886, Oct. 5, 1982) disclosed a mutant microorganism, *Pseudomonas putida* CB-173, that is capable of degrading phenolics at a temperature as low as 1° C. to 4° C. at a faster rate than known *Pseudomonas putida* type strains, and they disclosed a process for treating wastewater containing phenolics using the mutant microorganism strain. Molin and Nilssan disclosed a pseudomonad that is capable of growing in continuous culture with phenol as the only carbon and energy source under aerobic conditions (Molin, G. & Nilssan, I. *Degradation of phenol by Pseudomonas putida ATCC* 11172 *in continuous culture at different ratios of biofilm surface to culture volume, Applied and Environmental Microbiology,* 50, 946–950, 1985). Bossert et al. disclosed two bacterial species which utilize p-cresol as the sole source of carbon when grown in a co-culture of both microorganisms under nitrate-reducing conditions (Bossert, I. D., Rivera, M. D., & Young, L. Y. *p-Cresol biodegradation under denitrifying conditions: Isolation of a bacterial coculture, FEMS Microbiology Ecology,* 38, 313–319, 1986). A syntropic relationship was documented. Bossert and Young disclosed metabolism of p-cresol as a sole carbon source under nitrate-reducing conditions by the denitrifying bacterial isolate PC-07 (Bossert, I. D. & Young, L. Y. *Anaerobic oxidation of p-cresol by a denitrifying bacterium, Applied and Environmental Microbiology,* 52, 1117–1122, 1986). Nitrate was required as the external electron acceptor and was reduced to molecular nitrogen. Phenol, toluene, o-cresol and m-cresol were not metabolized by the isolate.

Tschech and Fuchs disclosed several strains of bacteria which, in the absence of molecular oxygen, oxidized phenol to carbon dioxide with nitrate as the terminal electron acceptor (Tschech, A. & Fuchs, G. *Anaerobic degradation of phenol by pure cultures of newly isolated denitrifying pseudomonads, Archives of Microbiology,* 148, 213–217, 1987). The bacteria were facultatively-anaerobic Gram-negative rods. Hu and Shieh disclosed removal of phenol and o-cresol under anoxic conditions in an upflow biofilter with nitrate as the electron acceptor (Hu, L. Z. & Shieh, W. K. *Anoxic biofilm degradation of monocyclic aromatic compounds, Biotechnology and Bioengineering,* 30, 1077–1083, 1987). O-cresol was removed at a slower rate. Major et al. disclosed the biodegradation of benzene, toluene and the isomers of xylene (formerly called BTX) in anaerobic batch microcosms containing shallow aquifer material. Denitrification was confirmed by nitrous oxide accumulation after acetylene blockage of nitrate reductase (Major, D. W., Mayfield, C. I., & Barker, J. F. *Biotransformation of benzene by denitrification in aquifer sand, Ground Water,* 26, 8–14, 1988). They proposed that the addition of nitrate to gasoline-contaminated aquifers would serve as an adjunct to current remedial techniques.

Kuhn et al. disclosed mineralization of toluene, m-xylene, m-cresol and p-cresol in an anaerobic laboratory aquifer column operated under continuous-flow conditions with nitrate as an electron acceptor (Kuhn, E. P., Zeyer, J., Eicher, P, & Schwarzenbach, R. P. *Anaerobic degradation of alkylated benzenes in denitrifying laboratory aquifer columns, Applied and Environmental Microbiology,* 54, 490–496, 1988). Benzene was not metabolized. Kuhn et al. also confirmed the mineralization of toluene, m-xylene, m-cresol and p-cresol by denitrifiers. Zache and Rehm disclosed the degradation of phenol by a defined mixed culture consisting of *Pseudomonas putida* F8 and *Cryptococcus elinovii* H1 under aerobic conditions (Zache & Rehm *Degradation of phenol by a coimmobilized entrapped mixed culture, Applied Microbial Biotechnology,* 30, 426–432, 1989). Häggbloin et al. disclosed metabolism of p-cresol under denitrifying conditions (Häggblom, M. M., Rivera, M. D., Bossert, I. D., Rogers, J. E., & Young, L. Y. *Anaerobic biodegradation of para-cresol under three reducing conditions, Microbial Ecology,* 20, 141–150, 1990). Phenol was utilized as a slower rate. Evans et al. isolated a denitrifying bacterium that grew on toluene as the sole source of carbon (Evans, P. J., Mang, D. T., Kim, K. S., & Young, L. Y. *Anaerobic degradation of toluene by a denitrifying bacterium, Applied and Environmental Microbiology,* 57, 1139–1145, 1991). Evans et al. documented the biotransformation of toluene, m-xylene and o-xylene under denitrifying conditions (Evans, P. J., Mang, D. T., & Young, L. Y. *Degradation of toluene and m-xylene and transformation of o-xylene by denitrifying enrichment cultures, Applied and Environmental Microbiology,* 57, 450–454, 1991). No transformation of benzene or p-xylene was reported. Hegeman and Nickens (in U.S. Pat. No. 5,024,949, Jun. 18, 1991) disclosed bacterium of the genus Pseudomonas which utilizes a branched chain alkyl-substituted aromatic hydrocarbon as its sole carbon and energy source, and which is capable of substantial degradation of trichlorethylene (TCE) under aerobic conditions. The bacterium was described as being capable of denitrification, but the electron donor during denitrification is undisclosed. Also disclosed were methods utilizing the bacterium for the detoxification of TCE-contaminated material. Hutchins disclosed biodegradation of toluene, ethyl benzene, m-xylene and o-xylene under nitrate-reducing conditions. Benzene was not degraded (Hutchins, S. R. *Biodegradation of monoaromatic hydrocarbons by aquifer microorganisms using oxygen, nitrate, or nitrous oxide as the terminal electron acceptor, Applied and Environmental Microbiology,* August, 2403–2407, 1991). Evans et al. isolated a nitrate-reducing bacterium (NRB), which they named Strain T1, that was capable of mineralization of toluene and o-xylene (Evans, P. J., Ling, W., Goldschmidt, B., Ritter, E. R., & Young, L. Y. *Metabolites formed during anaerobic transformation of toluene and o-xylene and their proposed relationship to the initial steps of toluene mineralization, Applied and Environmental Microbiology,* February, 496–501, 1992). Khoury et al. reported the anaerobic degradation of p-cresol by a denitrifying culture (Khoury, N., Dott, W. and Kampfer, P. *Anaerobic degradation of p-cresol in batch and continuous cultures by a denitrifying bacterial consortium, Applied and Environmental Biotechnology,* 37, February, 529–531, 1992) and the anaerobic degradation of phenol by a denitrifying culture (Khoury, N., Dott, W. and Kampfer, P. *Anaerobic degradation of phenol in batch and continuous cultures by a denitrifying bacterial consortium, Applied and Environmental Biotechnology,* 37, February, 524–528, 1992). Coschigano et al. disclosed the metabolism of toluene under denitrifying conditions by a constructed bacterial strain (Coschigano, P. W., Häggblom, M. M., & Young, L. Y. *Metabolism of both 4-Chlorobenzoate and Toluene under denitrifying conditions by a constructed bacterial strain, Applied and Environmental Microbiology,* 60, 989–995, 1994). Seyfried et al. reported that the denitrifying bacteria Pseudomonas sp. Strain T and Pseudomonas sp. Strain K172 oxidize toluene under denitrifying conditions, and that Strain T also oxidizes m-xylene (Seyfried, B., Glod, G., Schocher, R., Tschech, A., & Zeyer, J. *Initial reactions in the anaerobic oxidation of toluene and m-xylene by denitrifying bacteria, Applied and Environmental Microbiology,* 60, 4047–4052, 1994). Fries et al. characterized anaerobic toluene degradation under denitrifying conditions (Fries, M. R., Zhou, J., Chee-Sanford, J., & Tiedje, J. M. *Isolation characterization, and distribution of denitrifying toluene degraders from a variety of habitats, Applied and Environmental Microbiology,* 60, 2802–2810, 1994).

Dehalogenation by denitrifying cultures has also been reported. Bouwer and McCarty documented the dechlorination of carbon tetrachloride (CT), but not trichloroethane (TCA), under denitrifying conditions (Bouwer, E. J. & McCarty, P. L. *Transformations of 1- and 2-carbon halogenated aliphatic organic compounds under methanogenic conditions, Applied and Environmental Microbiology,* 45, 1286–1294, 1983). Egli et al. were unable to cause a hydrogen-oxidizing, autotrophic nitrate-reducing bacteria (NRB) to degrade CT (Egli, C., Tschan, T., Scholtz, R., Cook, A. M., & Leisinger, T. *Transformation of tetrachloromethane to dichloromethane and carbon dioxide by Acetobacterium woodii, Applied and Environmental Microbiology,* 54, 2819–2824, 1988). Criddle et al. isolated a denitrifying Pseudomonas sp. (strain KC) that is capable of dechlorinating CT (Criddle, C. S., DeWitt, J. T., Grbič-Galič, D., & McCarty, P. L. *Transformation of carbon tetrachloride by Pseudomonas sp. Strain KC under denitrification conditions. Applied and Environmental Microbiology,* 56, 3240–3246, 1990). Petersen et al. characterized a denitrifying consortium capable of transforming carbon tetrachloride (Petersen, J. N., Skeen, R. S., Amos, K. M., & Hooker, B. S. *Biological destruction of $CCl_4$: I. Experimental design and data, Biotechnology and Bioengineering,* 43, 521–528, 1994). Hooker et al. described kinetic modeling of biotransformation of carbon tetrachloride by a denitrifying consortium (Hooker, B. S., Skeen, R. S. and Petersen, J. N. *Biological destruction of $CCl_4$: II. Kinetic Modeling. Biotechnology and Bioengineering*, 44, 211–218, 1994). Skeen et al. described a batch reactor that they used to monitor biodegradation of carbon tetrachloride by a denitrifying culture (Skeen, R. S., Truex M. J., Petersen, J. N. and Hill, J. S. *A batch reactor for monitoring process dynamics during biodegradation of volatile organics. Environmental Process*, 13, 174–177, 1994).

Other background material is provided in a report by Yellowstone Environmental Science, Inc., of 920 Technology Blvd., Bozeman, Mont. 59715, entitled "Biomimetic Process for Hazardous Waste Remediation, Phase I Final Technical Report, August, 1992." That report is incorporated by reference herein as if fully set forth.

SUMMARY OF THE INVENTION

The present invention provides an apparatus and method for biodegradation of hydrocarbons dissolved in an aqueous matrix. Dissolved hydrocarbons include dissolved alkanes (saturated hydrocarbons), alkenes (unsaturated hydrocarbons), aromatic hydrocarbons and/or halogenated hydrocarbons. The aqueous matrix may be wastewater, groundwater, slurry or sludge. In one embodiment, the invention involves introducing an aqueous stream comprising at least one dissolved aromatic hydrocarbon (such as benzene, toluene, ethylbenzene, o-xylene, m-xylene, p-xylene, phenol, o-cresol, m-cresol, or p-cresol) and a dissolved oxide of nitrogen [such as nitrate ($NO_3^-$), nitrite ($NO_2^-$), nitric oxide (NO) and nitrous oxide ($N_2O$)] to a reactor, and operating said reactor under conditions that support denitrification of the aromatic hydrocarbon. In an alternative embodiment, the aqueous stream comprises at least one alkane (such as ethane) and/or at least one alkene (such as ethene or ethylene) and biodegradation of these compounds is accomplished. In a preferred embodiment, the aqueous stream also comprises at least one dissolved halogenated hydrocarbon [such as tetrachloroethylene (PCE), trichloroethylene (TCE), or 1,1,1-trichloroethane(TCA)] and dehalogenation of the halogenated hydrocarbon is accomplished. The reactor may be a continuous stirred tank reactor, a batch (or sequencing batch) reactor, a plug-flow reactor, a fixed-film reactor, a pore space in an underground aquifer, or another reactor configuration. The reactor is operated in such a way that molecular oxygen is excluded from the space or zone in which the biodegradation is occurring and the other requirements of denitrifying bacteria are met. In some embodiments, kinetic control (control of mean cell residence time) is used to enrich a denitrifying culture in the reactor.

The present invention relies on a reactor-engineering approach in the design of a bioremediation process, and overcomes the limitations of prior art methods and devices by providing an efficient and cost-effective apparatus and method for wastewater treatment and groundwater bioremediation. This invention is applicable to both of the following types of bioremediation modes: in situ (treated in place), or pump-and-treat (waste is pumped out of the ground, treated in a contained area above ground and pumped back underground). One object of the invention is to facilitate metabolism and co-metabolism of saturated hydrocarbons, unsaturated hydrocarbons, aromatic hydrocarbons and halogenated (e.g., chlorinated) hydrocarbons. Another object is to allow rational design of systems for anaerobic degradation of hydrocarbons. Further objects and advantages of the invention will become apparent from a consideration of the drawings and the ensuing description.

Figure 1:
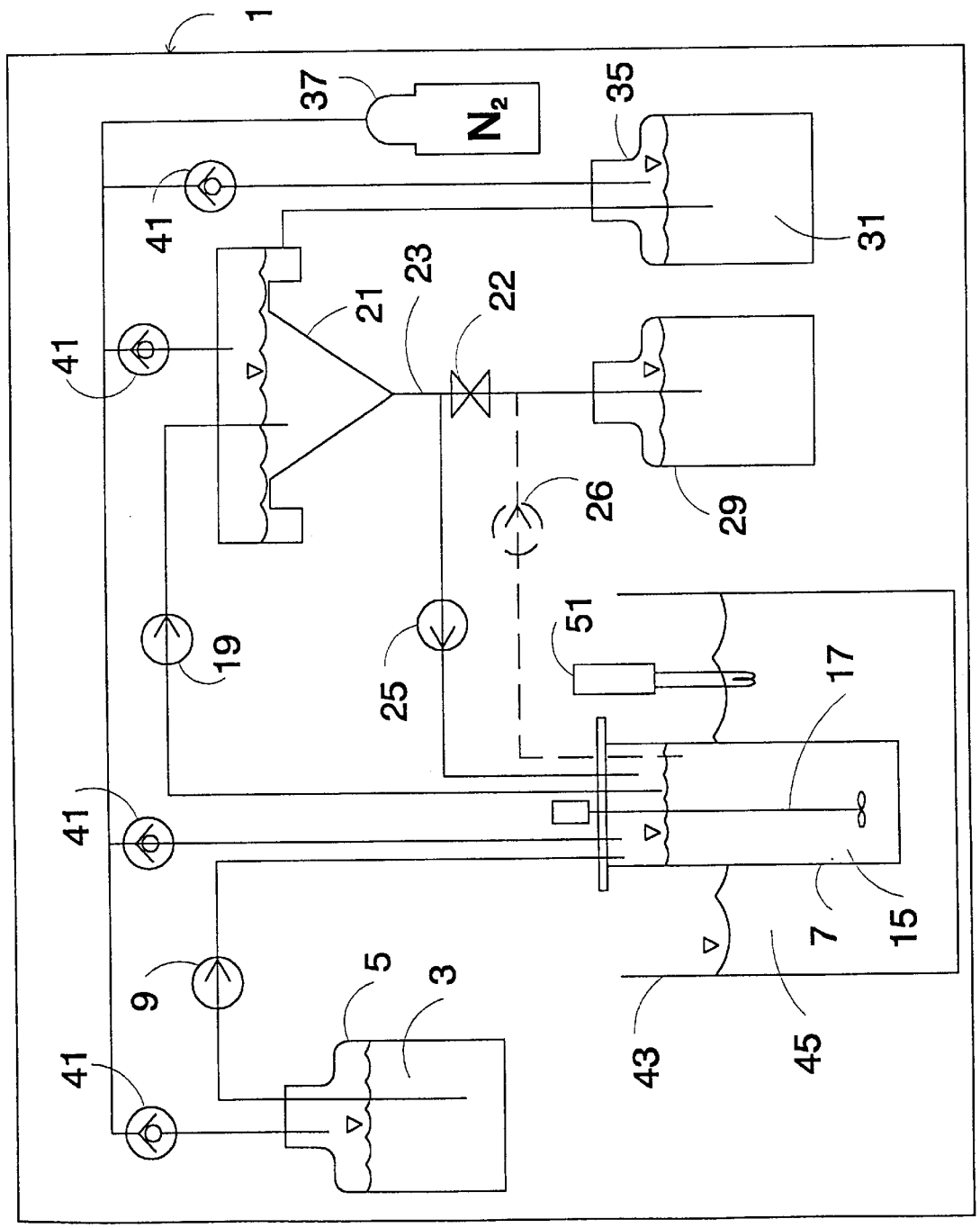
FIG. 1 is a schematic drawing of a first preferred embodiment of the apparatus and method.
Figure 4:
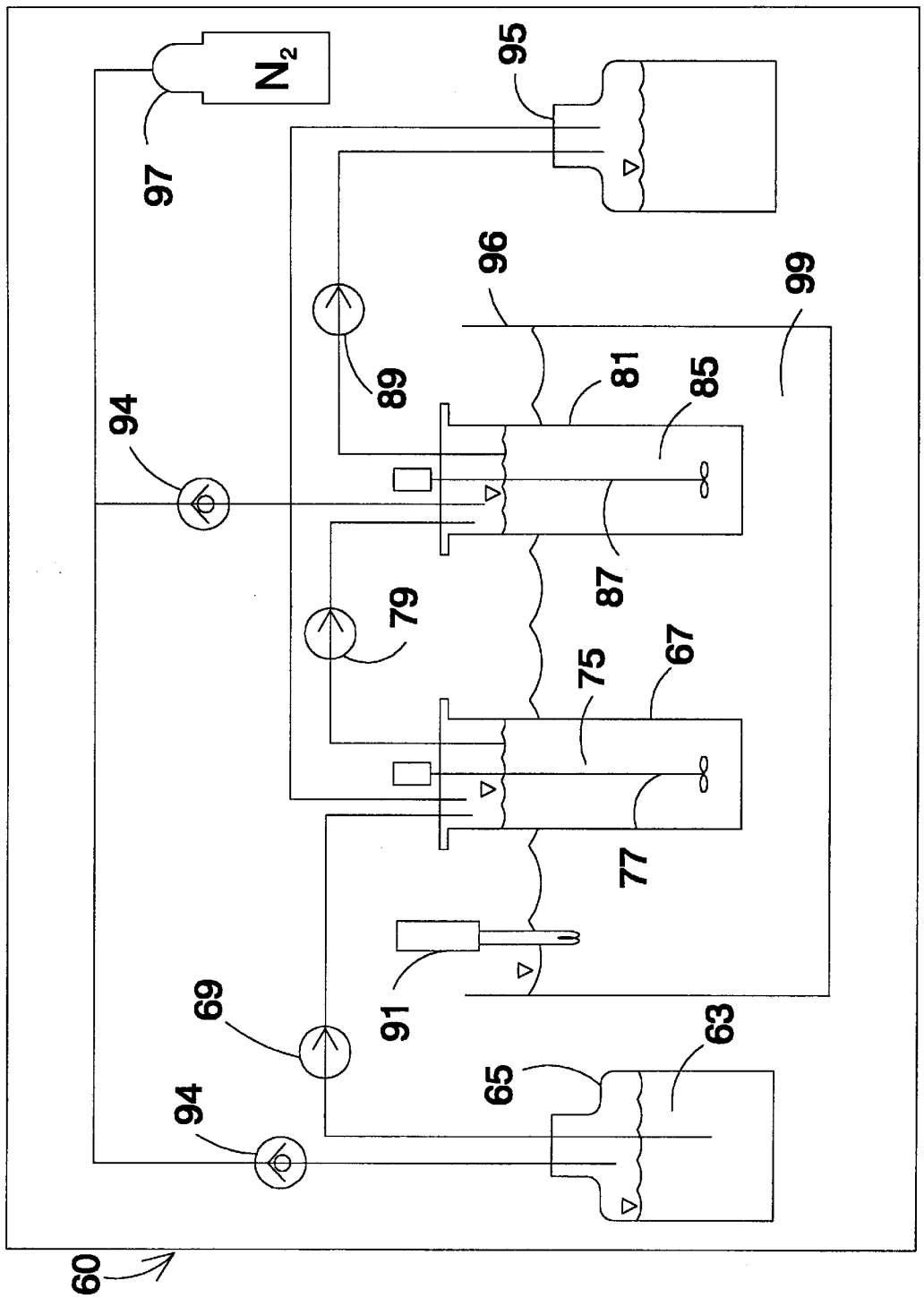
FIG. 4 is a schematic drawing of a second preferred embodiment of the apparatus and method.
Figure 5:
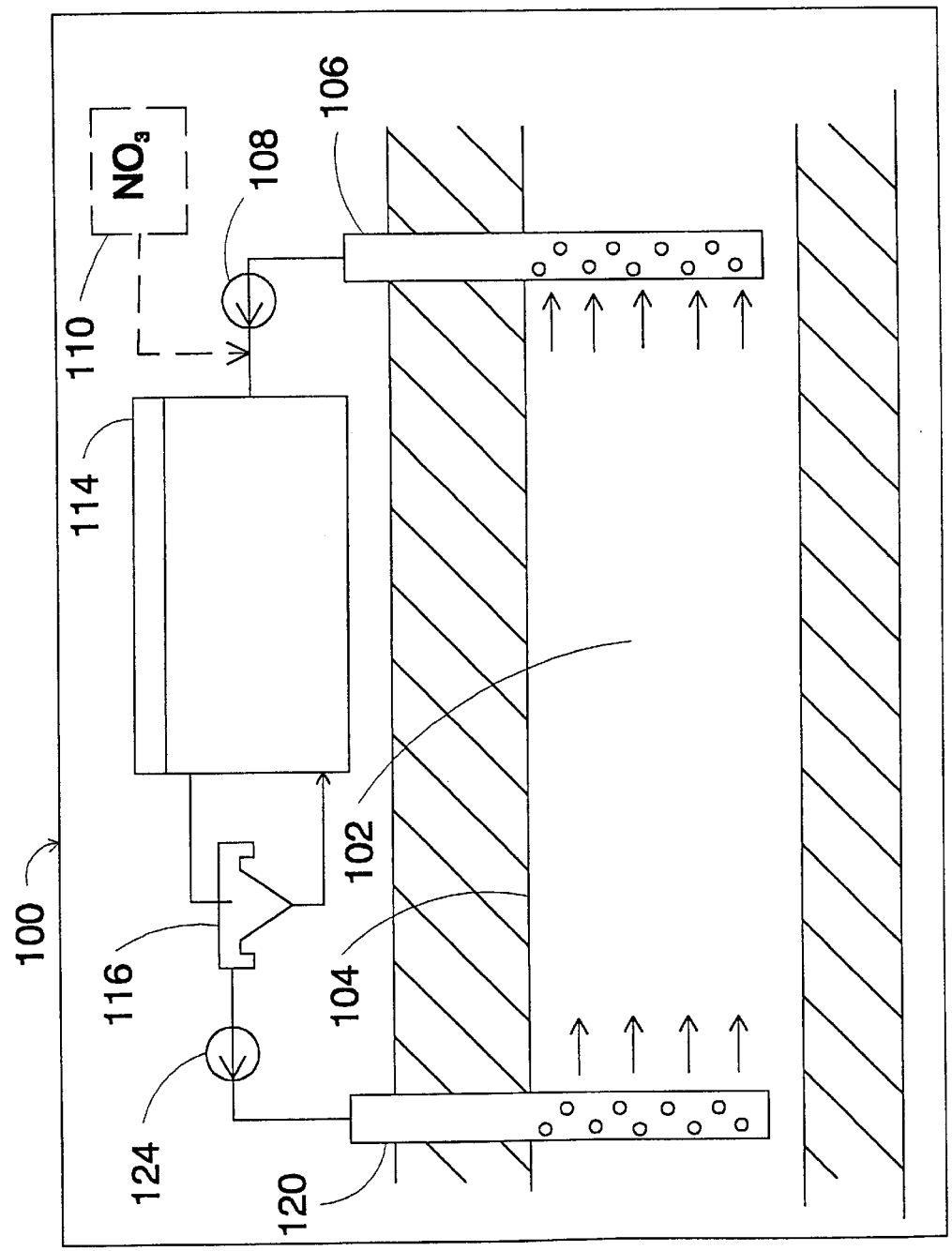
FIG. 5 is a schematic drawing of a third preferred embodiment of the apparatus and method.
Figure 6:
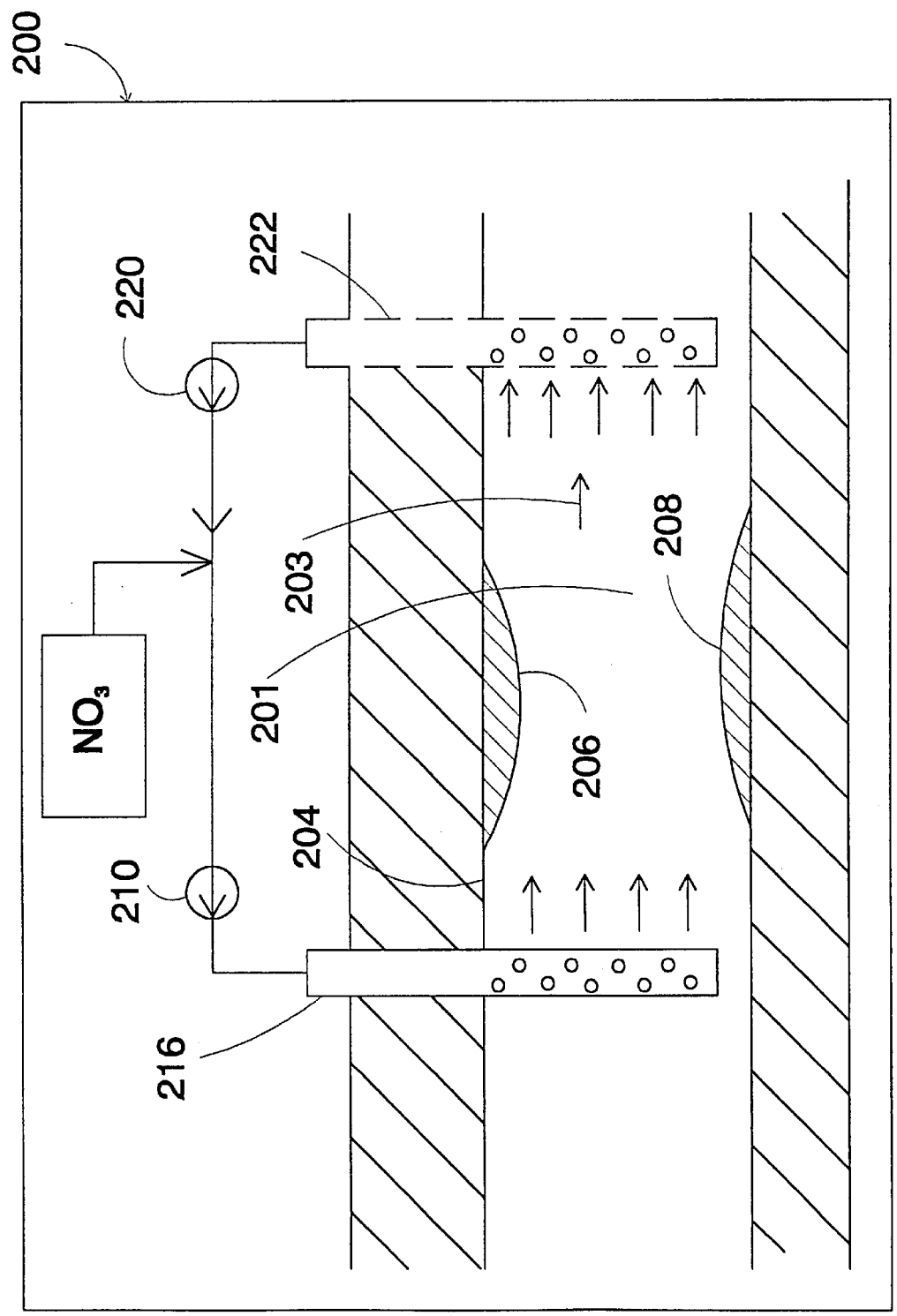
FIG. 6 is a schematic drawing of a fourth preferred embodiment of the apparatus and method.
Figure 7:
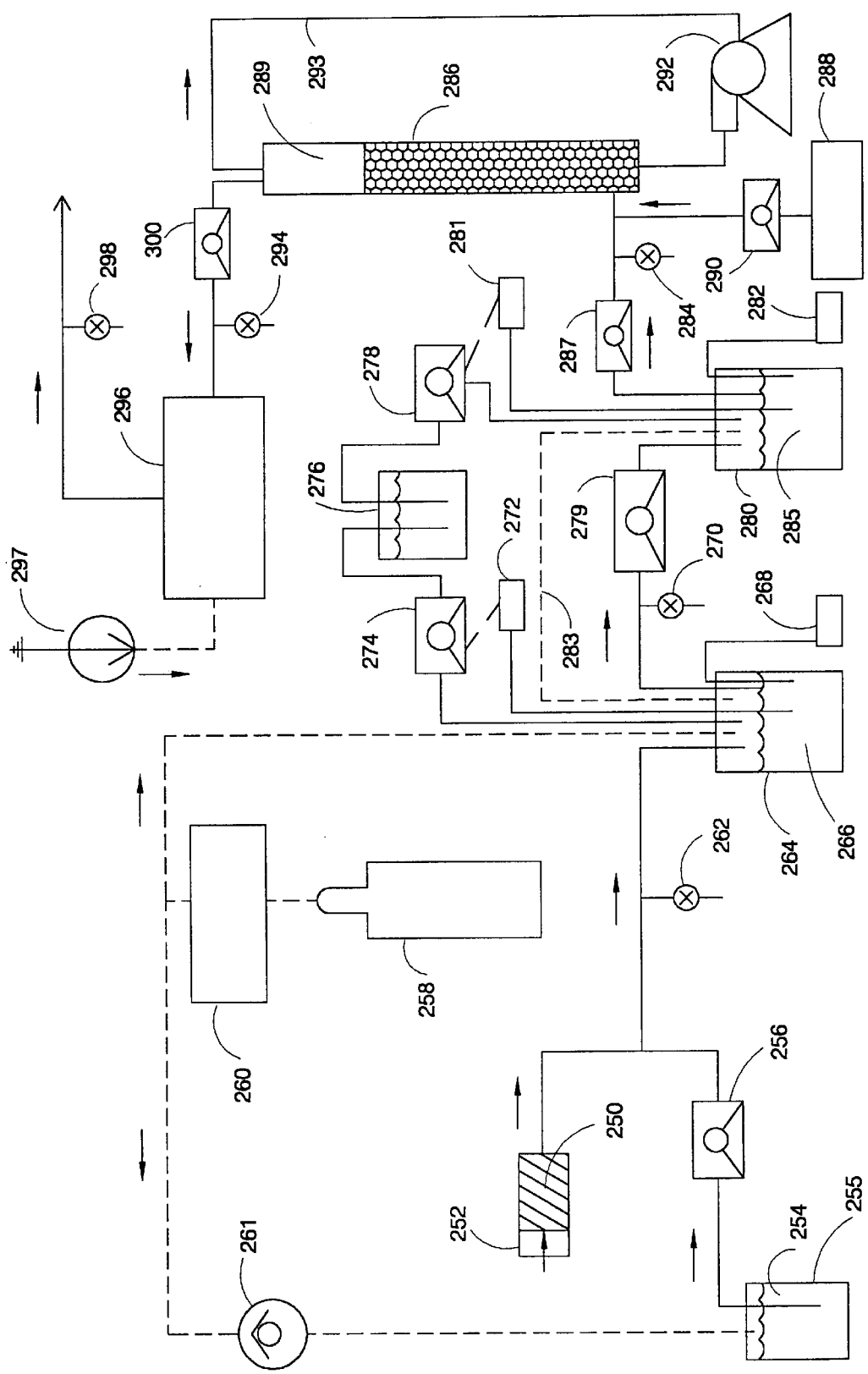
FIG. 7 is a schematic diagram of a working engineering prototype of the apparatus and method.

The following reference numbers are used to indicate the parts of the invention on the drawings:

FIG. 1:
1 apparatus
3 aqueous waste
5 influent container
7 growth reactor
9 pump
15 contents
17 stirrer
19 pump
21 sedimentation tank
22 valve
23 underflow
25 pump
26 pump
29 waste sludge container
31 clarified effluent
35 effluent container
37 oxygen-free nitrogen gas
41 check valves
43 tank
45 water
51 heater/circulator
FIG. 4:
60 apparatus
63 aqueous waste
65 influent container
67 first reactor
69 pump
75 first reactor contents
77 stirrer
79 pump
81 second reactor
85 second reactor contents
87 stirrer
89 pump
91 heater/circulator
94 check valves
95 effluent container
96 tank 97 oxygen-free nitrogen gas
99 water
FIG. 5:
100 apparatus
102 contaminated ground water
104 underground formation
106 extraction well
108 pump
110 dissolved nitrate
114 above-ground reactor
116 sedimentation tank
120 injection well
124 pump
FIG. 6:
200 apparatus
201 contaminated groundwater
203 direction of groundwater flow
204 underground formation
206 aromatic hydrocarbon
208 chlorinated hydrocarbon
210 pump
216 injection well
220 pump
222 extraction well
FIG. 7:
250 toxin solution
252 syringe pump
254 mineral medium
255 mineral medium container
256 first medium pump
258 compressed nitrogen gas cylinder
260 oxygen scrubber
261 check valve
262 first sample port
264 first denitrification chemostat
266 contents of first denitrification chemostat
268 first ORP monitor
270 second sample port
272 first pH monitor/controller
274 first acid pump
276 acid supply
278 second acid pump
279 second medium pump
280 second denitrification chemostat
281 second pH monitor/controller
282 second ORP monitor
283 gas equalizing tube
284 third sample port
285 contents of second denitrification chemostat
286 methanogenesis biofilm reactor
287 third medium pump
288 acetate solution
289 contents of methanogenesis biofilm reactor
290 fourth medium pump
292 recirculation pump
293 recirculation piping
294 fourth sample port
296 aerobic respiration chemostat
297 air compressor
298 fifth sample port
300 fifth medium pump

DESCRIPTION OF PREFERRED EMBODIMENTS

Referring to FIG. 1, apparatus 1 is being used to remove aromatic hydrocarbons and chlorinated hydrocarbons from aqueous waste 3. Aqueous waste 3 is transferred from influent container 5 to reactor 7 by pump 9. In a preferred embodiment, the contents 15 of reactor 7 are completely mixed by stirrer 17. Contents 15 are removed from reactor 7 by pump 19 and transferred to sedimentation tank 21 at the same rate that waste 3 is introduced into reactor 7. A portion of underflow 23 is returned (recycled) to reactor 7 by pump 25 and a portion is wasted via valve 22 to waste sludge container 29. Clarified effluent 31 flows from sedimentation tank 21 to effluent container 35. A positive pressure of oxygen-free nitrogen gas 37 is maintained on the headspaces of reactor 7, tank 21 and containers 5 and 35. Check valves 41 ensure that the headspaces are isolated from one another. In a preferred embodiment, reactor 7 is placed in tank 43 which contains water 45, the temperature of which is maintained by heater/circulator 51.

The rate, Q, at which waste 3 is introduced into reactor 7 and the rate at which contents 15 are removed from reactor 7 is controlled by the pumping rate of pump 9. In the absence of recycle (i.e., when the pumping rate of pump 25 is zero), the dilution rate (1) at which reactor 7 operates is related to the rate (Q) and the volume (V) of the amount of contents 15 in reactor 7 by the following expression:

$$D = Q/V \tag{1}$$

In this situation (as indicated in U.S. Pat. No. 5,076,927—the disclosure of which is incorporated herein by reference as if fully set forth), the mean cell residence time (MCRT) is related to rate (Q) and volume (V) as follows:

$$MCRT = V/Q \tag{2}$$

Thus, in the absence of cell recycle, a dilution rate or mean cell residence time is set by selecting an appropriate value for V relative to a given value of Q, or visa versa.

Referring again to FIG. 1, if wastage (removal of viable cells from the system) occurs only by the discharge of sedimentation tank underflow through valve 22, the MCRT is determined by the ratio of the concentration of viable cells in reactor 7 to that in the (underflow) recycle flow ($X/X_r$) and the ratio of the reactor volume (V) and the volumetric cell wastage rate ($Q_w$) as follows:

$$MCRT = (V/Q_w) * (X/X_r) \tag{3}$$

In an alternative embodiment, an alternative wastage scheme involves wastage directly from reactor 7 via pump 26. In this case, the concentration of cells in the wastage flow is the same as that in reactor 7 and the MCRT is calculated as follows:

$$MCRT = (V/Q_w) \tag{4}$$

A variety of empirical expressions have been proposed in the prior art to relate the specific growth rate of microorganisms to the concentration of limiting substrate to which they are exposed. A limiting substrate is the compound in a microorganism growth medium that limits the rate of growth of that microorganism in that medium. In the field of hazardous waste treatment, the limiting substrate is often the electron donor of the oxidation-reduction reaction catalyzed by the microorganism. For example, in the metabolism of toluene by a denitrifying microorganism culture that reduces nitrate to nitrogen gas, the following reaction is catalyzed:

$$5C_6H_5CH_5 + 36NO_3^- + 36H^+ \rightarrow 35CO_2 + 18N_2 + 38H_2O \quad (5)$$

The kinetics of microorganism growth is often expressed in terms of the specific growth rate ($\mu$) of the culture. The specific growth rate is defined as follows:

$$\mu = (dX/dt)/X \quad (6)$$

where:

$\mu$=the specific growth rate of the microorganism, dX/dt=the rate of change of the biomass concentration, and X=the biomass (viable cell) concentration at which growth is occurring.

In a CSTR supporting suspended growth, if effluent (cell) recycle is not practiced, the specific growth rate equals the dilution rate, and the MCRT is the reciprocal of $\mu$.

One of the most commonly used empirical expression for relating the microorganism specific growth rate ($\mu$) to the substrate concentration (S) is the Monod equation:

$$\mu = \mu_{max} * S/(S+K_s) \quad (7)$$

where:

$\mu_{max}$ is the maximum specific growth rate,

S is the substrate concentration, and $K_s$ is the half-saturation coefficient.

The term $\mu_{max}$ is a constant defined as the maximum value possible for $\mu$ under a specific set of conditions. $K_s$ determines how fast $\mu$ approaches $\mu_{max}$. $K_s$ is the substrate concentration at which $\mu$ is equal to one half of $\mu_{max}$. More complex models are used, but many of them reduce to the above "saturation-type" kinetic expression when growth inhibition is not important.

One empirical expression (among many available expressions) that is used in situations in which sufficiently high concentrations of limiting substrate are present in a growth medium (e.g., contents 15) to inhibit microorganism growth rates is the Luong inhibition function (Luong, J. H. T. *Generalization of Monod kinetics for analysis of growth data with substrate inhibition. Biotechnology and Bioengineering*, 29, 242–248, 1987):

$$\mu = \mu_{max} * S/(S+K_s) * (1-(S/S_m))^\alpha \quad (8)$$

where:

$S_m$=maximum allowable substrate concentration (e.g., concentration above which cells do not grow), and $\alpha$=model parameter.

Figure 2:
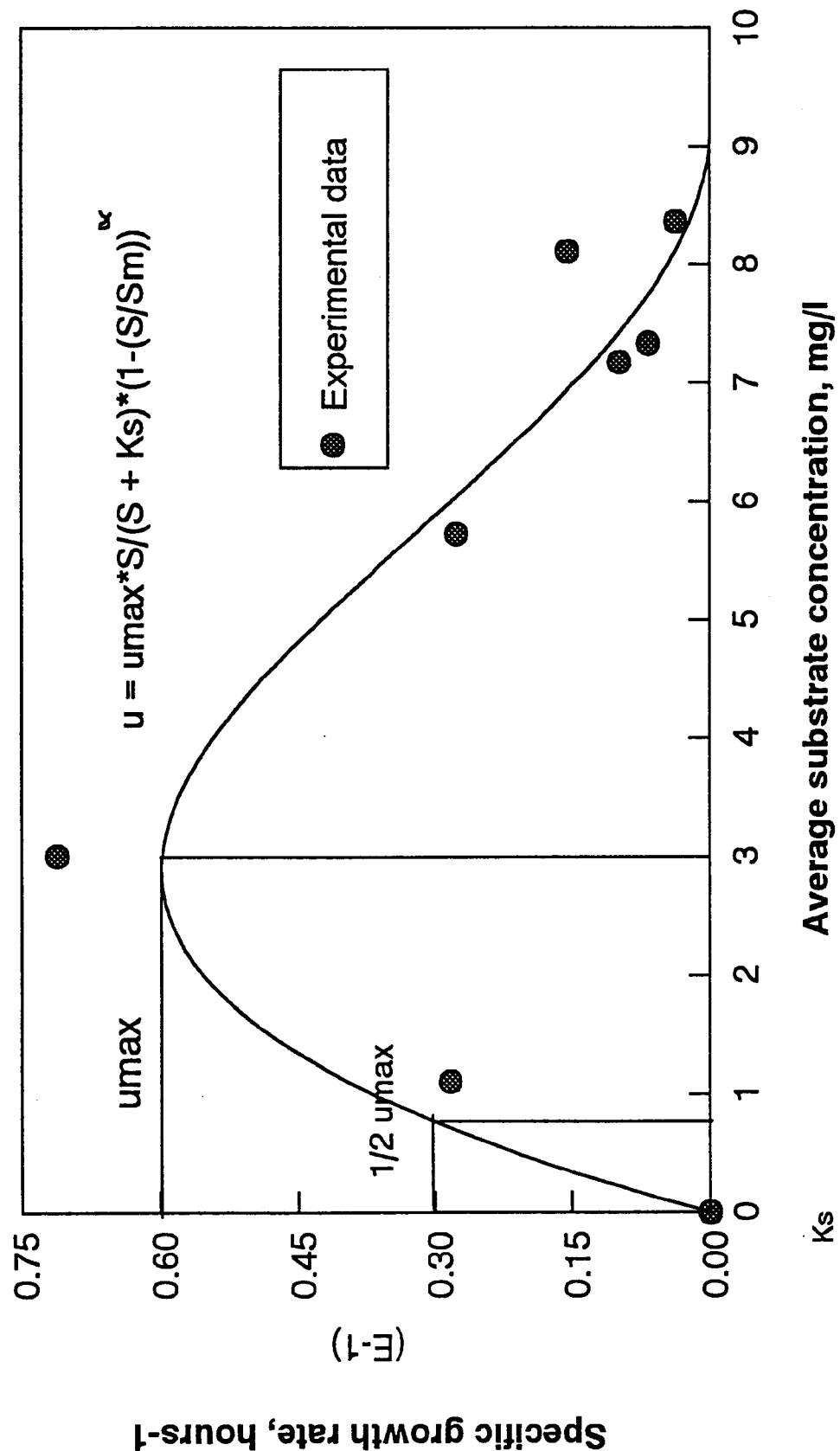
FIG. 2 is a plot characterizing denitrification with toluene metabolism.
Figure 3:
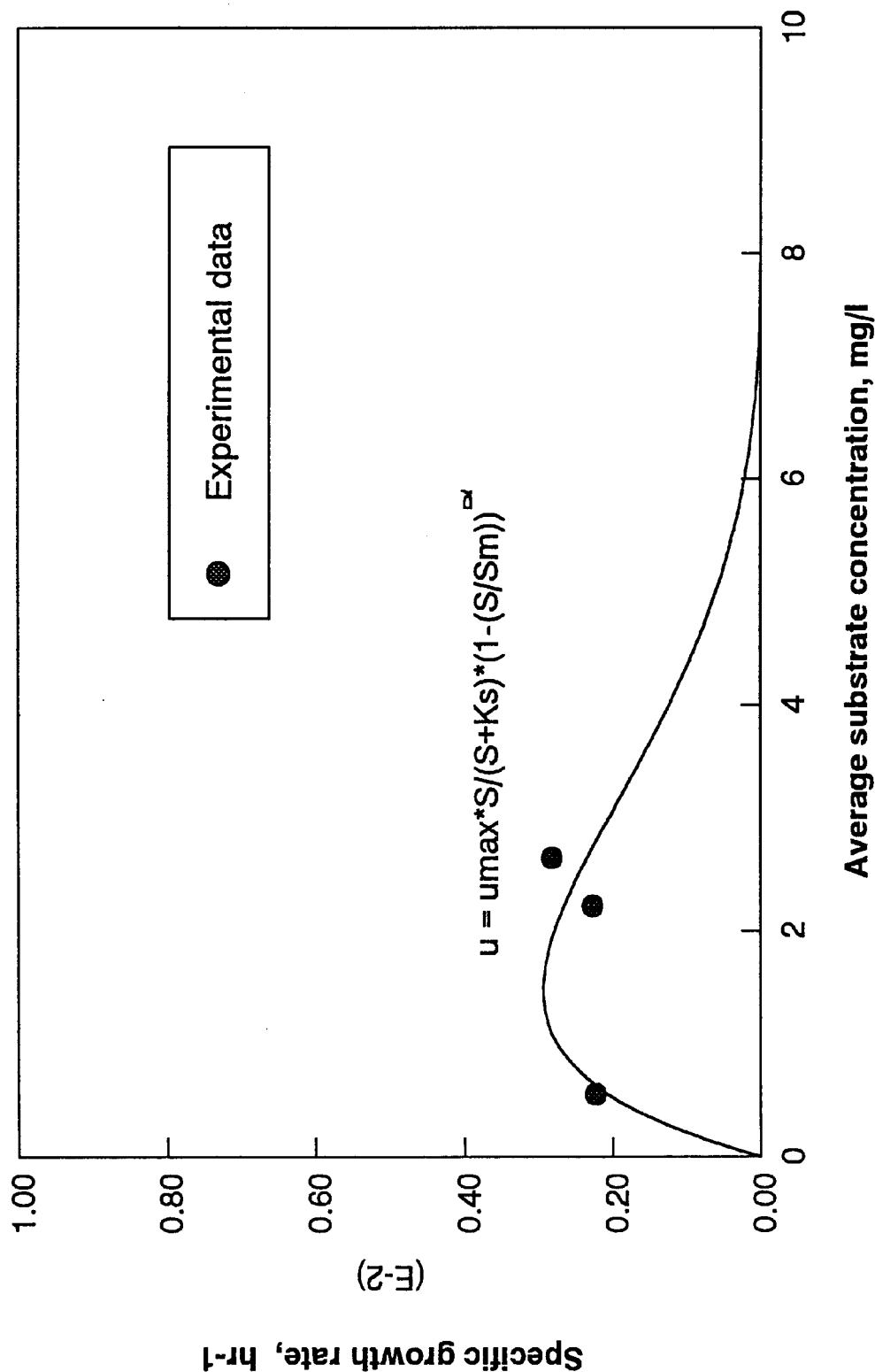
FIG. 3 is a plot characterizing denitrification with benzene metabolism.

The Luong inhibition function is used to characterize denitrification with toluene metabolism in FIG. 2 and denitrification with benzene metabolism in FIG. 3. Metabolism occurred at 35° C. in both instances.

Referring now to FIG. 2, the specific growth rate of the denitrifying culture increases to a maximum around 0.06 $hr^{-1}$ at a substrate (toluene) concentration of about 3 milligrams per liter (mg/l). At substrate concentrations below about 3 mg/l, an increase in substrate concentration results in an increase in specific growth rate. This would allow (cause) return to steady state (lower) concentration in a continuous stirred tank reactor (CSTR or chemostat), if for some reason, an increase in concentration were to occur. At substrate concentrations above about 3 mg/l, an increase in substrate concentration causes a decrease in specific growth rate, which in a CSTR would cause unstable operation and washout of the culture.

Referring now to FIG. 3, the specific growth rate of a denitrifying culture increases to a maximum of about 0.0027 $hr^{-1}$ at a substrate (benzene) concentration of about 1.5 mg/l. In a CSTR, stable growth would occur below a concentration of about 1.5 mg/l and washout would occur above that concentration.

In a preferred embodiment of the invention, an equation that relates specific growth rate to the substrate concentration in which growth is occurring is used to establish appropriate operating conditions for a reactor used to culture anaerobic bacterial cultures. For example, given a target toluene concentration for the contents (and, hence, effluent), we can substitute the following values into the Luong equation (equation 8 which was presented earlier in this application):

$\mu_{max}$=5.9 $hr^{-1}$ $K_s$=124 mg/l $S_m$=9.2 mg/l $\alpha$=2.144

This equation can then be used to select a dilution rate for a CSTR in which a denitrifying culture is accomplishing denitrification with toluene metabolism.

Thus, if a toluene effluent concentration of 0.1 mg/l is sought, a single CSTR should be operated at a dilution rate of about 0.005 $hr^{-1}$.

Similarly, given a target contents (and, hence, effluent) benzene concentration, equation 8 can be used to select a dilution rate for a CSTR in which a denitrifying culture is accomplishing denitrification with benzene metabolism, using the following values:

$\mu_{max}$=0.016 $hr^{-1}$ $K_s$=2.93 mg/l $S_m$=8.41 mg/l $\alpha$=3.117

Thus, if a benzene effluent concentration of 0.1 mg/l is sought, a single CSTR should be operated at a dilution rate of about 0.0005 $hr^{-1}$.

In alternative embodiments, reactor 7 is operated as a reactor configuration, the type of which could include one of the following reactor configurations: batch, sequencing batch, plug-flow or fixed-film. In these situations, different expressions are used to relate MCRT to effluent substrate concentration (effluent quality). Such expressions may be found in such standard texts as the following: 1) Grady, C., P., L., Jr. and Lim, H. C. (1980) *Biological Wastewater Treatment: Theory and Applications*. New York: Marcel Dekker; or 2) Bailey, J., E. and Ollis, D. F. (1986) *Biochemical Engineering Fundamentals*. New York: McGraw-Hill.

Referring now to FIG. 4, a second preferred embodiment of the invention is presented. In this embodiment, apparatus 60 is used to remove chlorinated hydrocarbons, alkanes and alkenes from aqueous waste 63. Aqueous waste 63 is transferred from influent container 65 to first reactor 67 by pump 69. In a preferred embodiment, the first reactor contents 75 of first reactor 67 are completely mixed by stirrer 77. First reactor contents 75 are removed from reactor 67 by pump 79 and transferred to second reactor 81 at the same rate that waste 63 is introduced into reactor 67. Second reactor contents 85 of second reactor 81 are completely mixed by stirrer 87. Second reactor contents 85 are pumped by pump 89 to effluent container 95. A positive pressure of oxygen-free nitrogen gas 97 is maintained on the headspaces of first reactor 67 and second reactor 81 and containers 65 and 95.

Check valves 94 ensure that the headspaces of reactors 67 and 81 and the headspace of effluent container 95 are isolated from the headspace of influent container 65. In a preferred embodiment, reactors 67 and 81 are placed in tank 96 which contains water 99, the temperature of which is maintained at 35° C. by heater/circulator 91.

Referring now to FIG. 5, a third preferred embodiment of the invention is presented. Apparatus 100 is used to pump and treat groundwater 102 from underground formation 104 that is contaminated with benzene. Contaminated groundwater 102 is extracted from underground formation 104 (e.g., a confined aquifer) through extraction well 106 by pump 108. In one embodiment, contaminated groundwater is supplemented with dissolved nitrate 110 and/or trace nutrients or vitamins. If contaminated groundwater 102 contains sufficient nitrate and other constituents to satisfy biodegradation stoichiometric requirements, it is introduced to above-ground reactor 114. Above-ground reactor 114 is operated at a temperature between 10° C. and 65° C. and at a MCRT of about 500 hours (±10 hours) to produce a benzene concentration of less than 1.0±0.1 mg/l. The volume of above-ground reactor 114 is minimized by recycling biomass settled out in sedimentation tank 116 back to reactor 114. Treated groundwater is returned to underground formation 104 through injection well 120 by pump 124.

Referring now to FIG. 6, a fourth preferred embodiment of the invention is presented. Apparatus 200 is used to bioremediate contaminated groundwater 201, which is moving in direction 203 in situ (in place) in the pore spaces of underground formation 204. Groundwater 201 is contaminated by dissolution of aromatic hydrocarbon 206 and chlorinated hydrocarbon 208 (a dense nonaqueous phase liquid) into groundwater 201 as it flows by pockets of concentrated or neat hydrocarbons 206 and 208. In one embodiment, contaminated groundwater 201 is augmented with dissolved nitrate and/or trace elements or vitamins needed from growth of denitrifying organisms by means of pump 210 and injection well 216, located upgradient from the source of pollution. In an alternative embodiment, contaminated groundwater 201 is extracted from underground formation 204 through extraction well 222 (which is located downgradient from the source of pollution) by pump 220, and is supplemented with dissolved nitrate and/or trace nutrients or vitamins and returned to underground formation 204 through well 216 by pump 210.

Apparatus 200 is operated to ensure that the dissolved toluene concentration in contaminated groundwater in the pore spaces of at least a portion of underground formation is less than about 10 mg/l. In a preferred embodiment, this is accomplished by recirculating (recycling) treated groundwater containing a relatively low concentration of dissolved toluene to the reactor (zone of in situ bioremediation).

Refer now to FIG. 7, which is a schematic diagram of the prototype. Oxygen-free nitrogen gas was used to pressurize first denitrification chemostat 264, second denitrification chemostat 280, reactor 286 and mineral medium container 255. The gas supply was comprised of compressed gas cylinder 258, oxygen scrubber 260 and check valve 261. Said check valve 261 prevented microorganism-contaminated gas from entering the mineral medium container 255 from other parts of the system.

First denitrification chemostat 264 was fed with an influent mixture comprised of concentrated toxin solution 250 supplied by adjustable-rate syringe pump 252 and mineral medium 254 supplied by adjustable-rate first medium pump 256. First sample port 262 provided a mechanism for obtaining samples of said influent mixture prior to changes in toxin concentrations caused by biological activity within the system.

First and second denitrifying chemostats 264 and 280 were kept at constant temperature with an adjustable-temperature water bath (not shown). The constant-pH control system of reactor 264 was comprised of first pH monitor/controller 272, first acid pump 274 and acid supply 276. Said pH control system automatically added acid to the chemostat in order to keep the contents 266 within a user-defined pH range. In order to confirm that anaerobic conditions were maintained within the reactor 264, the oxidation-reduction potential of said contents 266 was measured and displayed via first ORP monitor 268.

Effluent from chemostat 264 was supplied to second denitrifying chemostat 280 via second medium pump 279. Samples of said effluent were collected via second sample port 270 for analysis by external instruments (not shown). Headspace gases in chemostats 264 and 280 were connected through gas equalizing tube 283. The constant-pH control system of chemostat 280 was comprised of second pH monitor/controller 281, second acid pump 278 and acid supply 276. Said pH control system automatically added acid to chemostat 280 in order to keep the contents 285 of chemostat 280 within a user-defined pH range. In order to confirm that anaerobic conditions were maintained within the reactor 280, the oxidation-reduction potential of said contents 285 was measured and displayed via second ORP monitor 282.

Effluent from chemostat 280 was supplied to methanogenesis biofilm reactor 286 by third medium pump 287. Samples of said effluent were collected via third sample port 284. Acetate 288 was supplied to reactor 286 via fourth medium pump 290. The contents 289 of reactor 286 were recirculated through said reactor 286 via recirculation pump 292. The said contents 289 were maintained at a constant, user-defined temperature by placing a portion of the recirculation piping 293 in a constant-temperature water bath (not shown).

Effluent from reactor 286 was supplied to aerobic respiration chemostat 296 by fifth medium pump 300. Said effluent was sampled via fourth sample port 294. Atmospheric air was supplied to chemostat 296 via air compressor 297. Effluent from chemostat 296 was sampled via fifth sample port 298 prior to entering a conventional waste containment or treatment system (not shown).

WORKING EXAMPLE

An engineering prototype was designed to demonstrate the removal of the aromatic hydrocarbons (benzene, ethylbenzene, toluene, xylenes, phenol and cresols) and the chlorinated hydrocarbons (PCE, TCE and TCA) from a simulated waste stream. Design of the prototype was based on the results of the bioprocess model parameter estimation studies of a denitrifying culture that is capable of degradation of a variety of dissolved hydrocarbons. The denitrifying culture, identified as YES01, was obtained by enrichment over a 1+year period in a low-dilution rate chemostat inoculated with biological material obtained from a variety of hazardous waste sites. The chemostat was fed with a medium that contained aromatic hydrocarbons and chlorinated hydrocarbons. The culture was deposited with accession number ATCC 55712 under U.S. Patent and Trademark Office rules with the American Type Culture Collection (ATTC) on Sep. 20, 1995, which was during the pendency of the patent application of this application. After deposit, the culture can be obtained from the American Type Culture Collection, 12301 Parklawn Drive, Rockville, Md. 20852-1776, tel#: 1-800-638-6597, fax#: 1-301-231-5826.

The Phase II prototype was designed to demonstrate the removal of the aromatic hydrocarbons (benzene, ethylbenzene, toluene, xylenes, phenol and cresols) and the chlorinated hydrocarbons (PCE, TCE and TCA) from a simulated waste stream. Based on the results of the model parameter estimation studies, the inventors decided to incorporate a denitrification step, a methanogenesis step and an aerobic respiration step into the prototype. The following pages present a description of the studies conducted to design the prototype, the specifications used in each of the three design steps for the prototype, and the experimental results of the prototype.

Note: While other investigators have documented the capabilities of sulfate-reducing cultures to degrade certain hydrocarbons (Aeckersberg et al., 1991; Edwards et al., 1992; Beller et al., 1992; Rabus et al., 1993), a sulfate reduction step was not included in the prototype because during the model parameter estimation studies, enrichment of a sulfate-reducing culture with appropriate capabilities eluded the inventors.

Denitrification Step

Kinetic data from batch suspended growth studies were used in designing the denitrification step. The Luong inhibition model (Luong, 1987) was fitted to the results of the benzene and toluene studies in order to obtain parameters for initial design. For initial calculations, the single continuous stirred tank reactor (CSTR) model with a single soluble substrate utilizing Monod kinetics was used. Use of a CSTR and Monod kinetics is appropriate if the reactor is operated at a dilution rate at which substrate inhibition does not occur, as was the case here.

The Monod model (Monod, 1949) states that the specific growth rate of microorganisms is related to the concentration of the growth limiting substrate in the media as follows:

$$\mu = \mu_{max} S/(K_s+S) \tag{9}$$

where:

$\mu$=specific growth rate, hr$^{-1}$, $\mu_{max}$=maximum specific growth rate, S=limiting substrate concentration, and $K_x$=half saturation constant.

Recalling the definition of hydraulic residence time, $\tau$=V/Q, where V is the volume of the reactor and Q is the flow rate (Grady & Lim, 1980), the following equation may be derived:

$$\mu = \gamma + 1/\tau + b \tag{10}$$

where $\mu$=specific growth rate, hr$^{-1}$, $\gamma$=specific death rate coefficient, hr$^{-1}$, and b=maintenance coefficient, hr$^{-1}$.

Since $\gamma$ and b are relatively constant and relatively small (compared to $\mu$) for a given population of microbes under a given environment, the growth rate $\mu$ is controlled only by the residence time $\tau$. The cell residence time is thereby controlled by adjusting either the volume of the CSTR or the flow rate entering the CSTR. Substituting equation (10) into equation (9), the effect of the residence time ($\tau$) on the concentration of a single soluble substrate may be seen:

$$S = K_x(\gamma+1/\tau+b)/[\mu_{max}-(1/\tau+\gamma+b)] \tag{11}$$

Essentially this equation states that the concentration of soluble substrate in a CSTR can be controlled by varying $\tau$, if $\gamma$ and b are constant. The influent concentration $S_o$ does not appear in the equation, so the concentration of the chemostat at any time t is not affected by $S_o$.

As $\tau$ becomes very large, the specific growth rate equals the sum of the specific rates of maintenance and decay. Thus, there is a minimum substrate concentration that can be achieved with a single CSTR, described by:

$$S_{min}=K_s(\gamma+b)/[\mu_{max}-(\gamma+b)] \tag{12}$$

In our studies, parameters were taken from the Luong model utilizing benzene as the substrate because benzene is the most recalcitrant aromatic hydrocarbon compound, which means it is the slowest to be degraded. The parameters needed were $\mu_{max}$, $K_s$, b and $Y_g$. The maintenance coefficient b, and the true growth yield coefficient $Y_g$ were obtained from toluene degradation studies because these parameters could not be derived for benzene.

Applying the parameters gained from the Luong model to equation 12, a minimum concentration of benzene of 4.4 mg/l was found. This did not meet the specifications for target effluent concentrations. Therefore, a single CSTR model was not used for the working prototype.

Since a single reactor could not obtain low enough concentrations of substrate, the inventors evaluated the use of a series of denitrification reactors. A chain of reactors is capable of achieving a lower substrate concentration than a single reactor of equal volume. In any reactor after the first, growth is not needed to balance death and decay, since organisms are added in the feed. A two-stage series of chemostats were evaluated, because larger series of CSTR's become complex and difficult to model, and offer no real advantage in reducing effluent concentrations after a third reactor (Grady & Lim, 1980). Growth rates become increasingly slow in resulting chemostats, so a two-chemostat model was selected for the prototype.

A multiple CSTR model was evaluated using the procedure presented by Grady & Lim (1980). Several equations must be used in calculating the effluent concentrations of the first and second chemostats. Equation 13 describes the concentration of viable cells ($X_v$) in the reactor:

$$X_v = Y_g(S_o-S)/[(1+\gamma\tau+b\tau)] \tag{13}$$

where $Y_g$=true growth yield, $S_o$=influent substrate concentration,

S=concentration of substrate in the reactor, $\gamma$=death rate coefficient, $\tau$=cell residence time, and b=maintenance coefficient.

Another equation is needed to describe the effluent concentrations of multiple reactors. Equation 14 describes the concentrations of substrate in reactors 1 and 2:

$$[\mu_{max}-(1/\tau+\gamma+b)]S_2^2-[\mu_{max}(X_{v1}/Y_g+S_1)+(K_s-S_1)(1/\tau+\gamma+b)]S_2+ \\ S_1K_s(1/\tau+\gamma+b)=0 \tag{14}$$

where $S_1$, $S_2$=substrate concentrations in the first and second reactors, and $X_{v1}$=concentration of viable cells in reactor 1.

The following trial and error procedure was used, substituting equation 13 into equation 14, to find effluent concentrations from reactors 1 and 2. First, a dilution rate was assumed, and the effluent concentration of reactor 1 was found with equation 12. Next, the viable cell concentration in the first chemostat was determined and used in equation 14 to find the effluent concentration of the second chemostat. After a number of iterations, a dilution rate $D=0.003$ $hr^{-1}$ was reached that met our effluent concentration criteria of 0.1 mg/l for each aromatic hydrocarbon. Care was taken so that the substrate concentration in the first chemostat did not inhibit the microbes. The residence time where cell washout occurs was also checked to prevent washout of the cultures before reaching essentially complete degradation of the substrate. The following equation from Grady & Lim (1980) describes cell washout:

$$T_{min}=(K_s+S_o)/[S_o(\mu_{max}-\gamma-b)-K_s(\gamma+b)] \quad (15)$$

where $T_{min}$=minimum residence time at which cell washout occurs.

In order for all of the constituents in the denitrification step to be degraded, the nitrate required in the media for metabolism was needed. Stoichiometries from the metabolism reactions presented in the inventor's Phase I Final Report (Hunter et al., 1992) were used to calculate the amount of nitrate ($NO^-_3$) needed for essentially complete metabolism of all substrates present in the influent. This value of $NO^-_3$ was reduced by a factor of two, because the inventors did not expect all compounds to be degraded before the methanogenic step. The $NO^-_3$ concentration was subsequently modified by trial and error during the experiments to essentially eliminate it from the effluent of the denitrification step.

The prototype included a media stream which was designed to be added to a toxin stream and mixed before entering the reactor. The media flow rate was 0.25 ml/min. Toxins were placed in a syringe pump designed at a flow rate of 0.25 µl/min. When added together, the toxin and media flows produced the required dilution rate of 0.003 $hr^{-1}$.

The design of the apparatus addressed anaerobic concerns by using oxygen-impermeable and corrosion-resistant materials (e.g., glass, butyl rubber, Teflon® and 316 stainless steel). Sample ports were placed at each influent and effluent stream of both denitrification chemostats. A zero headspace was maintained in the sample ports to prevent volatilization of the toxins.

The denitrification step of the demonstration prototype consisted of two five-liter working volume chemostats connected in series. The reactors were housed in a 30° C. constant-temperature water bath. An independent oxygen-free nitrogen system supplied a positive pressure of approximately one psig to the reactors. A multi-channel Orion Expandable Ion Analyzer was used to continually monitor pH, ORP and temperature within the reactors. Liquid sampling ports were provided in the influent tubing prior to the first chemostat, prior to the second chemostat and following the second chemostat; this allowed monitoring of toxin concentrations at each stage in the process.

The cultures in the reactors were started from the same denitrification enrichment cultures from which the inoculum for all kinetic experiments was originally taken. The first reactor was filled with two liters of the enrichment culture and three liters of denitrification media (see Tables 1 and 2) and run in batch mode. The pH was adjusted to 7.0 and reductant was added until the ORP was less than −300 millivolts (i.e., until the resazurin indicator was clear). After the culture was grown in batch for several days, the media flow and toxins were placed on-line and the chemostat received the influent waste stream (day 1) consisting of mineral media, diluted toxins and a small amount of methanol (from the concentrated toxin standards) at a flow rate of 0.25 ml/min. The effluent from the first reactor was directed into the second reactor (day 12), which was maintained on batch until the liquid level reached five liters, which took approximately two weeks (day 26). The two denitrification chemostats were run for another twenty-one days to determine that the electron acceptor ($NO_3^-$) level was low enough to prevent takeover of the methanogenic reactor by the denitrifying consortium. Nitrate levels were reduced to 100 mg/l as nitrogen in the effluent of the second denitrification chemostat during the prototype operation. After the nitrate levels were reduced, the effluent was directed into the methanogenic step and the system was placed on continuous flow mode (day 47). During the demonstration run, samples were periodically taken from each of the three sampling ports and analyzed by gas and ion chromatography.

TABLE 1

Mineral Solution for Denitrification Media

| Constituents | Concentration, mg/l |
| --- | --- |
| Potassium phosphate (monobasic), $KH_2PO_4$ | 870 |
| Potassium phosphate (dibasic), $K_2HPO_4$ | 540 |
| Potassium nitrate, $KNO_3$ | 5,000 |
| Ammonium sulfate, $(NH_4)_2SO_4$ | 1,000 |
| Magnesium sulfate, $MgSO_4.7H_2O$ | 200 |

TABLE 2

Trace Mineral Solution Used in Preparation of Denitrification Medium

| Constituent[a] | Concentration, mg/l[b] |
| --- | --- |
| Calcium sulfate dihydrate, $CaSO_4.2H_2O$ | 200 |
| Iron (II) sulfate heptahydrate, $FeSO_4.7H_2O$ | 100 |
| Manganese (II) sulfate monohydrate, $MnSO_4.H_2O$ | 50 |
| Sodium molybdate (VI) dihydrate, $NaMoO_4.2H_2O$ | 10 |
| Copper (II) sulfate pentahydrate, $CuSO_4.5H_2O$ | 10 |
| Sulfuric acid, 0.1N $H_2SO_4$ | 100 ml |

[a]10 ml added to 1000 ml of mineral solution.
[b]Except as noted.

Methanogenesis Step

Both kinetic control (control of mean cell residence time) and electron acceptor ($NO^-_3$) concentration control was used to separate the denitrifying and methanogenic cultures. Thus, even though carbon dioxide was available as an electron acceptor in the denitrification reactors, methanogens could not colonize the denitrification reactor because the dilution rate was too high and $NO^-_3$ was available. Because a long mean cell residence time was sought in the methanogenic step, a combination suspended growth/fixed film reactor was developed. The methanogenic reactor was designed to be capable of operation in both upflow and downflow modes, but only the upflow mode was demonstrated.

In designing the methanogenic reactor, extreme care was taken to ensure conditions were anaerobic, because oxygen is very toxic to methanogens. Ports used in the prototype were composed of butyl rubber, glass, Teflon®, Kynar® and 316 stainless steel. Glass was used for the main reactor cylinder while Teflon®, Kynar and 316 stainless steel were used for the piping in the recirculation system. Teflon® was also used for both the top and bottom flow diverter caps. The larger volume of the methanogen reactor resulted in more surface area to which the toxins could potentially adsorb or adhere, so high-quality impermeable components were needed for accurate results.

Because resource constraints did not allow the inventors to develop intrinsic kinetic and stoichiometric model parameters for dechlorination during this project, the methanogenic reactor was designed using kinetic and stoichiometric data from the literature. For design purposes, the (conservative) assumption was made that all dechlorination would occur in the methanogenic reactor. Because PCE and its breakdown products were considered the most recalcitrant compounds, the reactors were specifically designed to remove them.

Tandol et al. (Tandol, V., DiStefano, T. D., Bowser, P. A., Gossett, J. M., & Zinder, S. H. *Reductive dehalogenation of chlorinated ethenes and halogenated ethanes by a high-rate anaerobic enrichment culture, Environ. Sci. Technol.*, 28, 973–979, 1994) found that PCE and its breakdown products were dechlorinated by a methanogenic culture via the following two reactions in series:

$$PCE \rightarrow VC \rightarrow ETH \qquad (16)$$

They developed dechlorination rates for an anaerobic enrichment culture that used methanol and acetate as electron donors during dechlorination of up to 90 mg/l of PCE. Since effluent PCE concentrations sought during this project were much less than the $K_m$ proposed by Tandol et al. (1.66 mg/l), and in order to simplify the design process, first order approximations were used as follows:

$$-r_{PCE} = (V_m/K_m)C_{PCE} \qquad (17)$$

where:

$$V_m/K_m = k_{PCE} = 1.25/1.0 = 1.25 \ hr^{-1} - r_{VC} = (V_m/K_m)C_{VC} \qquad (18)$$

where:

$V_m/K_m = k_{VC} = 0.06 \ hr^{-1}$

Assuming that: 1) a similar dechlorinating suspended biomass concentration could be achieved in the Phase II prototype [about 180 mg/l of total solids or 90 mg/l of total organic carbon (TOC)], and 2) that all dechlorination occurs in the suspended biomass, the CSTR effluent concentrations © of PCE and VC [with an assumed influent PCE concentration of 1.0 mg/l and a detention time ($\tau$) of 400 hours (D=0.0025 $hr^{-1}$)] were estimated as follows (Grady & Lim, 1980):

$$C_{PCE} = C_{PCE0}/(1+k_{PCE}\tau) = 1.0/(1+1.25)(400) = 0.002 \ mg/l \qquad (19)$$

$$C_{VC} = C_{VC0}/(1+k_{VC}\tau) + [k_{PCE}C_{PCE0}\tau/(1+k_{PCE}\tau)(1+k_{VC}\tau)] \qquad (20)$$

$$= 0.0/(1+0.06*400) + [1.25*1.0*400/(1+1.25*400)(1+0.06*400)] = 0.95 \ mg/l \qquad (21)$$

The biomass that was incorporated into a biofilm in the reactor had a much longer detention time, thereby reducing chlorinated hydrocarbon concentrations further. Although this addition removal could also be modeled, available resources did not allow further rationalization of the design.

Thus, the methanogenic reactor was designed with a working volume (empty) of eight liters allowing a lower dilution rate (D=0.0025 $hr^{-1}$) than the denitrification reactors. A lower dilution rate was needed because methanogens grow slower than denitrifiers. In addition, the reactor was designed as a completely mixed reactor since high recirculation rates induced complete mixing of the liquid contents of the reactor. A very small headspace of 30–50 ml was provided in the methanogenic reactor to minimize any volatilization that would occur with a large headspace.

The methanogenic reactor comprised a four-foot-long 3½-inch inside diameter (ID) glass tube filled to a depth of 17 inches, with 3-mm diameter Ballotini glass beads to provide a large surface area (about 37,000 $cm^2$) for microbe attachment. The large surface area of the beads allowed for a greater biofilm/reactor volume ratio in order to increase substrate consumption. Recirculation of the media was achieved with a 2-horsepower Atlas Model C pump. Media was pumped through 1-inch ID Teflon® tubing at eight gallons per minute, a rate sufficient to suspend the beads without shearing off the microbes. The upflow design was used so that clogging of the bed did not occur. Microbes attach readily at the dilution rates which the upflow design accomplishes.

The ends of the reactor were designed so that the flow moved uniformly through the reactor. The effluent port required essentially zero flow and no pressure, so a flow diverter cap was designed for the top of the glass tube. Approximately 99.5 percent (calculated by dividing the effluent flowrate by the recirculation flowrate) of the liquid contents of the reactor was recycled through the recirculation loop. The bottom end-cap of the glass tube was designed so that a uniform velocity profile moved into and through the column of beads.

During the initial testing of the methanogenic reactor, heat produced by the recirculation pump increased the heat of the reactor to 66° C., which was too hot for stable methanogen growth. Thus, an in-line heat exchanger was built from two meters of stainless ⅝-inch tubing and connected to the recirculation loop. With the heat exchanger immersed in a 13° C. water bath, the reactor temperature stabilized at a temperature 33.8° C. and 35° C.

A supplementary stream of dissolved acetate was provided as a primary substrate in order to support cometabolism of the halogenated hydrocarbons. A flow of 0.05 ml/min was used to keep the dilution of the methanogenic reactor at 0.0025 $hr^{-1}$. Acetate was supplied through a syringe pump at a concentration of 1,300 mg/l (after day 32). In addition, other methanogen medium constituents were supplied through the acetate stream (see Table 3).

TABLE 3

Methanogenesis Mineral Media for Prototype Demonstration

| Constituent | Concentration (mg/l) |
|---|---|
| Ammonium bicarbonate, $NH_4HCO_3$ | 15,000 |
| Ammonium chloride, $NH_4Cl$ | 900 |
| Calcium chloride, $CaCl_2.2H_2O$ | 600 |
| Magnesium chloride, $MgCl_2.6H_2O$ | 850 |
| Potassium phosphate (dibasic), $K_2HPO_4$ | 2,250 |
| Sodium chloride, NaCl | 400 |
| Acetic acid (dry, acetate only), $CH_3CO_2Na.3H_2O$ | 1,300 |
| Trace element solution | 10 ml/l |
| Vitamin solution | 10 ml/l |
| Reductant | 5 ml |

Sampling ports were provided at both the influent and effluent ends of the methanogenic reactor. These allowed for determination of the removal efficiency of the methanogenic reactor alone (single pass efficiency), and also that of the whole system including the denitrification reactors.

The reactor utilized three-mm glass beads as attachment substrate. The minimal headspace was supplied with oxygen-free nitrogen through the same nitrogen tank as the denitrification reactors. A system of check valves was used to isolate the headspaces of the denitrification reactors from the headspace of the methanogenic reactor. Temperature was monitored by an inline thermometer and maintained at approximately 35° C. by a cooling loop within the system. The pH and ORP were monitored daily and adjusted manually. Liquid sampling ports were located prior to the influent and in the effluent stream of the methanogenic reactor.

In order to prepare the reactor for inoculation, the empty volume was continuously purged with oxygen-free nitrogen for at least 30 minutes, and finally pressurized to 5 psi. The reactor was then filled with oxygen-free methanogenic mineral media (refer to Tables 4 to 6) by pumping from a closed, anaerobic system. Ten milliliters of concentrated resazurin solution were then added to the reactor. The pH was adjusted to neutral, and reductant (see Table 7) was added to the system until the media was reduced (the resazurin turned clear). The reactor flow was turned on and the system was run abiotically to ensure maintenance of reduced conditions. After the reactor remained clear over a period of several days, approximately two liters of inoculum from the methanogenic enrichment and 500 ml of *Methanosarcina vacuolata* (ATCC 35090) culture, which was obtained from American Type Culture Collection, were anaerobically inoculated into the pre-reduced medium. The reactor flow was turned off for 48 hours to allow the cells to adhere to the substrate. The beads and Teflon® components of the reactor quickly took on a characteristic black color, and cells were seen in samples viewed under a microscope. The reactor flow was turned on (day 20) and run in batch mode for several more days.

TABLE 4

Mineral Solution Used in Preparation of Methanogenic Medium

| Constituent | Concentration, mg/l |
| --- | --- |
| Ammonium bicarbonate, $NH_4HCO_3$ | 3,000 |
| Ammonium chloride, $NH_4Cl$ | 180 |
| Calcium chloride, $CaCl_2.2H_2O$ | 120 |
| Magnesium chloride, $MgCl_2.6H_2O$ | 170 |
| Potassium phosphate (dibasic), $K_2HPO_4$ | 450 |
| Potassium phosphate (monobasic), $KH_2PO_4$ | 450 |
| Sodium chloride, NaCl | 900 |
| Yeast extract | 1,000 |

TABLE 5

Trace Element Solution Used in Preparation of Methanogenic Medium

| Constituent[a] | Concentration, mg/l |
| --- | --- |
| Boric acid, $H_3BO_3$ | 100 |
| Cobalt chloride, $CoCl_2.6H_2O$ | 1,000 |
| Copper chloride, $CuCl_2.2H_2O$ | 80 |
| Ferric chloride, $FeCl_3.6H_2O$ | 20,000 |
| Manganese chloride, $MnCl_2.4H_2O$ | 6,000 |
| Sodium molybdnate, $Na_2MoO_4.2H_2O$ | 100 |
| Zinc chloride, $ZnCl_2$ | 80 |

[a]One ml added to 1,000 ml of mineral solution.

TABLE 6

Vitamin Solution Used in Preparation of Methanogenic Medium

| Constituent[a] | Concentration, mg/l |
| --- | --- |
| para-Aminobenzoic acid | 50 |
| Biotin | 50 |
| Cobalamin | 5 |
| Folic acid | 20 |
| Nicotinic acid | 50 |
| Pyridoxine hydrochloride | 100 |
| Riboflavin | 50 |
| Thiamine hydrochloride | 50 |

[a]One ml added to 1,000 ml of mineral solution.

TABLE 7

Reductant Solution

| Constituent[a] | Concentration, mg/l |
| --- | --- |
| Resazurin | 300 |
| Sodium dithionite, $Na_2S_2O_4$ | 1,000 |
| Sodium sulfide, $Na_2S.9H_2O$ | 12,000 |

[a]Five ml added to 1,000 ml of mineral media solutions.

Finally, media, toxins and acetate were directed into the reactor. An initial 53.3 microliters ($\mu$l) of 15 g/l TCE,TCA, and PCE solution (on day 27) were injected into the methanogenic reactor to provide an initial concentration of 0.1 mg/l in the reactor of these constituents. A separate 1,000 mg/l solution of TCE, PCE, and TCA was directed into the reactor at a flow of 0.25 $\mu$l/min (on day 32). An acetate and mineral media (shown earlier in Table 3) was placed in another syringe pump at a flow of 0.05 ml/min. The methanogenic reactor was operated separate from the denitrification reactors for 3 weeks until all reactors were connected for the demonstration effort. At this time (day 47), the chlorinated hydrocarbons were removed from the influent of the methanogenic reactor, whereas the inventors used the toxins in the influent to the denitrification steps. During the demonstration effort, samples were taken daily and monitored by gas chromatography for toxin content.

Aerobic Respiration Step

A sealed aerobic chemostat with a working volume of five liters was provided to polish the methanogenic reactor effluent and remove any residual substrate that was not utilized in the denitrification and methanogenic steps. A model 400 Whisper air pump was used to aerate the aerobic chemostat. The flow rate into the aerobic reactor was designed to be the same rate as the methanogenic reactor effluent, about 0.30 ml/min. This produced a dilution rate of 0.0036 $hr^{-1}$. Analysis of the system was performed before and after the aerobic respiration step to determine the efficiency of the anaerobic components of the system prior to the aerobic polishing step.

The waste stream treated by the Phase II prototype was formulated to mimic a typical hazardous waste stream containing aromatic hydrocarbons and solvents. Characteristic averages of these constituents in actual industrial waste streams and contaminated waters were determined through a review of published data. The target influent concentration of each constituent was set at 100 mg/l of each of the following aromatic hydrocarbons: benzene, toluene, ethylbenzene, m-xylene, o-xylene, p-xylene, phenol, m-cresol, o-cresol and p-cresol; and one mg/l each of the following chlorinated hydrocarbon solvents: TCE, TCA and PCE. In order to achieve these concentrations in the influent, concentrated solutions of 100 g/l benzene, toluene, ethylbenzene and xylene (called BTEX); 50 g/l phenol and cresols and 10 g/l of the chlorinated solvents were injected from a syringe pump through $\frac{1}{16}$-inch inner diameter Teflon® tubing directly into the mineral medium flow (after day 59). Flow rates of the toxins and the media were set to dilute the toxins to the target influent concentrations within the total medium flow. A chronology of the operation of the prototype is presented in Table 8.

When all of the process components were connected in series, the aerobic reactor was attached as a final polishing step (day 47). The aerobic component consisted of a single five-liter CSTR housed in the 30° C. water bath. The effluent from the methanogenic reactor was directed as influent into the reactor at a flow rate of 0.30 ml/min., which provided a dilution rate of 0.0036 hr$^{-1}$. The reactor was supplied with oxygen by a small air pump which drew from the laboratory air supply. Environmental parameters such as pH and temperature were manually monitored and adjusted daily. A sampling port was installed directly in the effluent line.

The reactor was inoculated with four liters of effluent from the two denitrification reactors and one liter of culture from the aerobic enrichment. The inoculum was transferred into the reactor and the contents were purged and operated in batch mode. The pH was adjusted to neutral and the air supply was connected During the demonstration run, samples were taken daily and analyzed by means of gas chromatography to monitor toxin concentrations and evaluate the performance of the entire system.

TABLE 8

Chronology of Prototype Operation

| Day | Action taken |
|---|---|
| 1 | Denitrification chemostat no. 1 started in continuous flow mode. Calculated influent toxin concentrations were 50 mg/l of each aromatic hydrocarbon and 0.5 mg/l of each chlorinated hydrocarbon. |
| 12 | Overflow into and filling of denitrification chemostat no. 2 in fed batch mode begun. |
| 20 | Methanogenic reactor started in batch mode. |
| 26 | Denitrification chemostat no. 2 filling completed; continuous flow begun. |
| 27 | 0.1 mg/l each of PCE, TCE and TCA added to methanogenic reactor. |
| 32 | Continuous flow to methanogenic reactor begun. Calculated influent toxin concentrations were 1.0 mg/l of each chlorinated hydrocarbon. |
| 42 | Reduced concentration of nitrate influent by two-thirds. |
| 47 | All reactors connected. Toxin addition rates adjusted to produce calculated influent toxin concentrations of 200 mg/l for each BTEX compound, 100 mg/l of phenol and each cresol and 2.0 mg/l of each chlorinated hydrocarbon. |
| 48 | Influent and effluent samples collected and analyzed by YES. |
| 52 | PCE, TCE and TCA addition rates increased to produce calculated influent concen. of 4.0 mg/l of each. Influent and effluent samples collected and analyzed by YES. |
| 54 | Influent and effluent samples collected by YES and analyzed by an independent lab. |
| 56 | Influent and effluent samples collected and analyzed by YES. |

TABLE 8-continued

Chronology of Prototype Operation

| Day | Action taken |
|---|---|
| 59 | PCE, TCE and TCA addition rates increased to produce calculated influent concentrations of 20.0 mg/l of each. Influent tubing changed to Viton. |
| 63 | Influent and effluent samples collected by YES and analyzed by YES and independent laboratory. |
| 67 | Influent and effluent samples collected by YES and analyzed by YES and by independent laboratory. |
| 74 | Influent and effluent samples collected by YES and analyzed by independent laboratory. |

Experimental Results of Working Model

Samples were taken daily from each sampling port in order to monitor toxins by gas chromatography and nitrate by ion chromatography. The BTEX phenol and cresol gas chromatography samples were taken with a gas tight syringe, filtered with a 2-$\mu$m millipore filter to remove biomass and dispensed into 0.5-ml serum bottles. The bottles were immediately crimp capped with Teflon®-faced butyl rubber stoppers. The samples were then analyzed for toxin concentrations on a Hewlett Packard 5890-series II gas chromatograph equipped with a flame ionization detector. Gas chromatography samples for chlorinated solvents were taken with a gastight syringe and extracted into pentane (10-mil liquid sample into one-ml pentane). The samples were agitated for 20 minutes and the pentane fraction was removed and dispensed into a 0.5 ml serum bottle. The samples were analyzed on a Hewlett Packard 5890-series II gas chromatograph equipped with a Hall electrolytic conductivity detector. Samples for ion chromatography were taken with a gastight syringe, filtered with a two-$\mu$m millipore filter and dispensed into two-ml screw cap vials. The samples were analyzed on a Dionex Ion Chromatograph.

Figure 8:
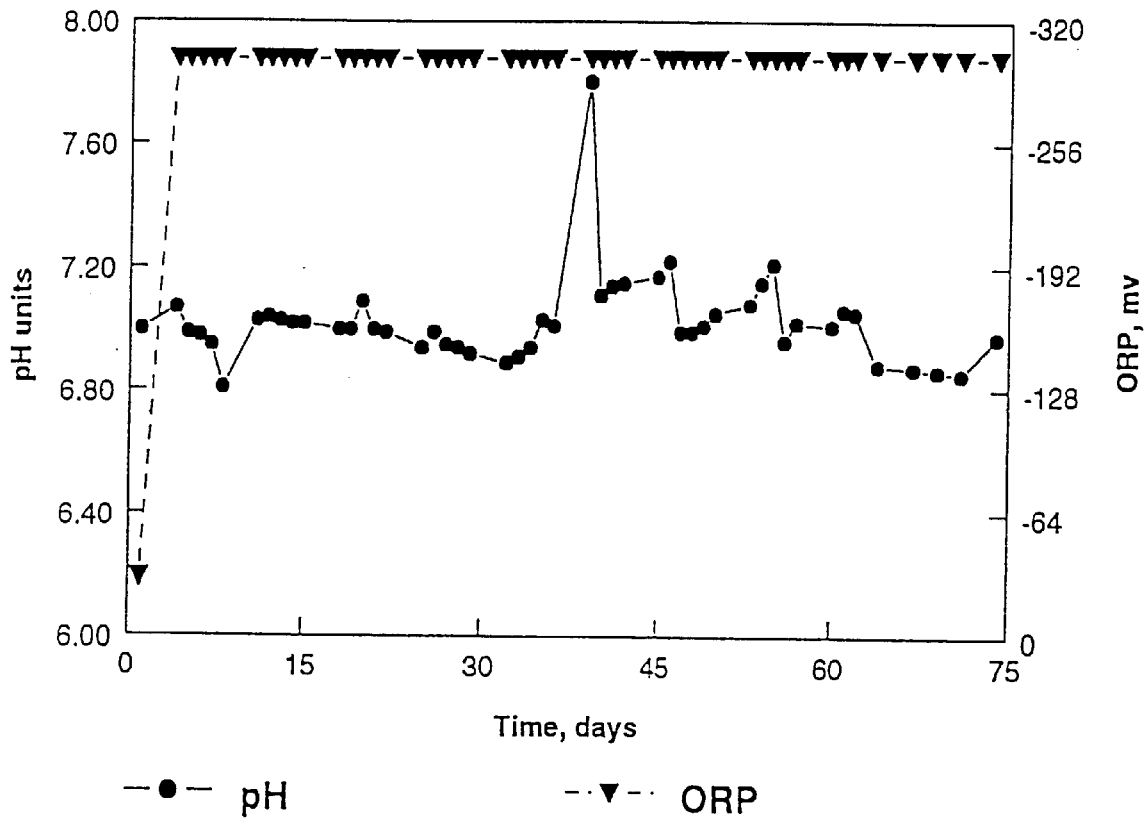
FIG. 8 is a graph representing the environmental conditions inside the first denitrification reactor and illustrates the changes in pH and ORP.
Figure 9:
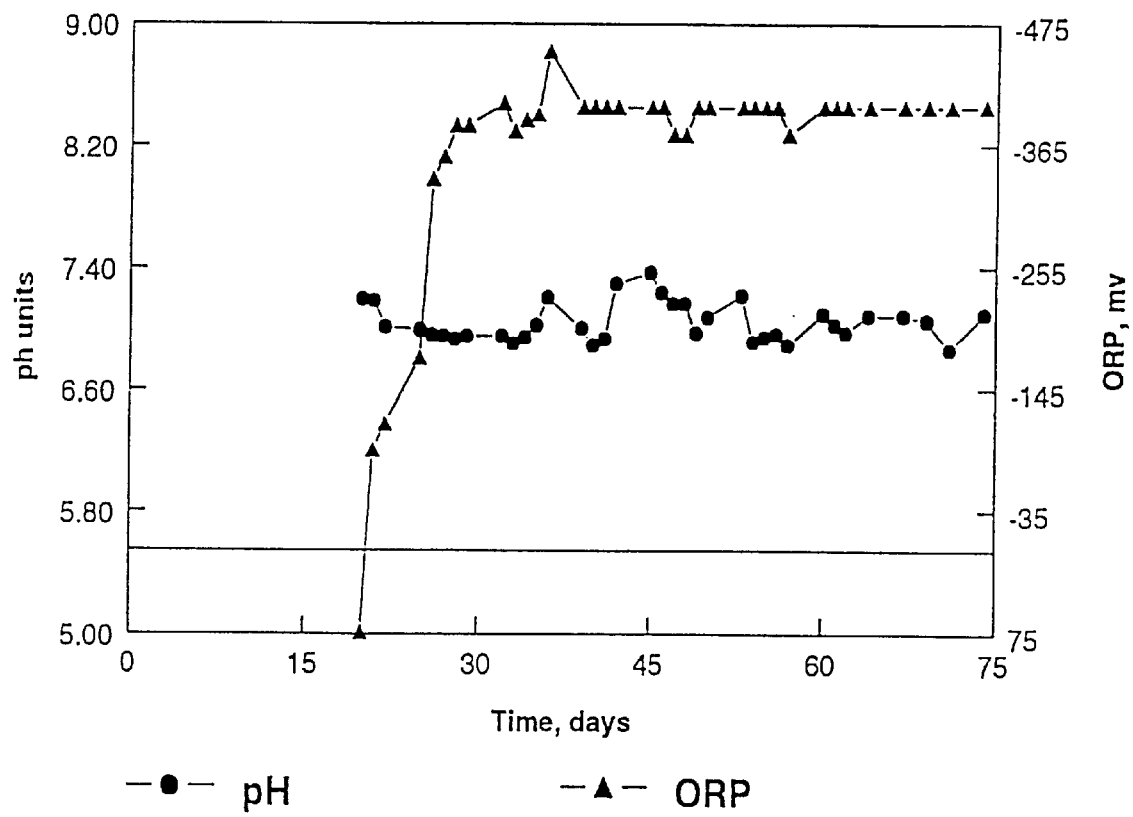
FIG. 9 is a graph representing the environmental conditions inside the second denitrification reactor and illustrates the changes in pH and ORP.
Figure 10:
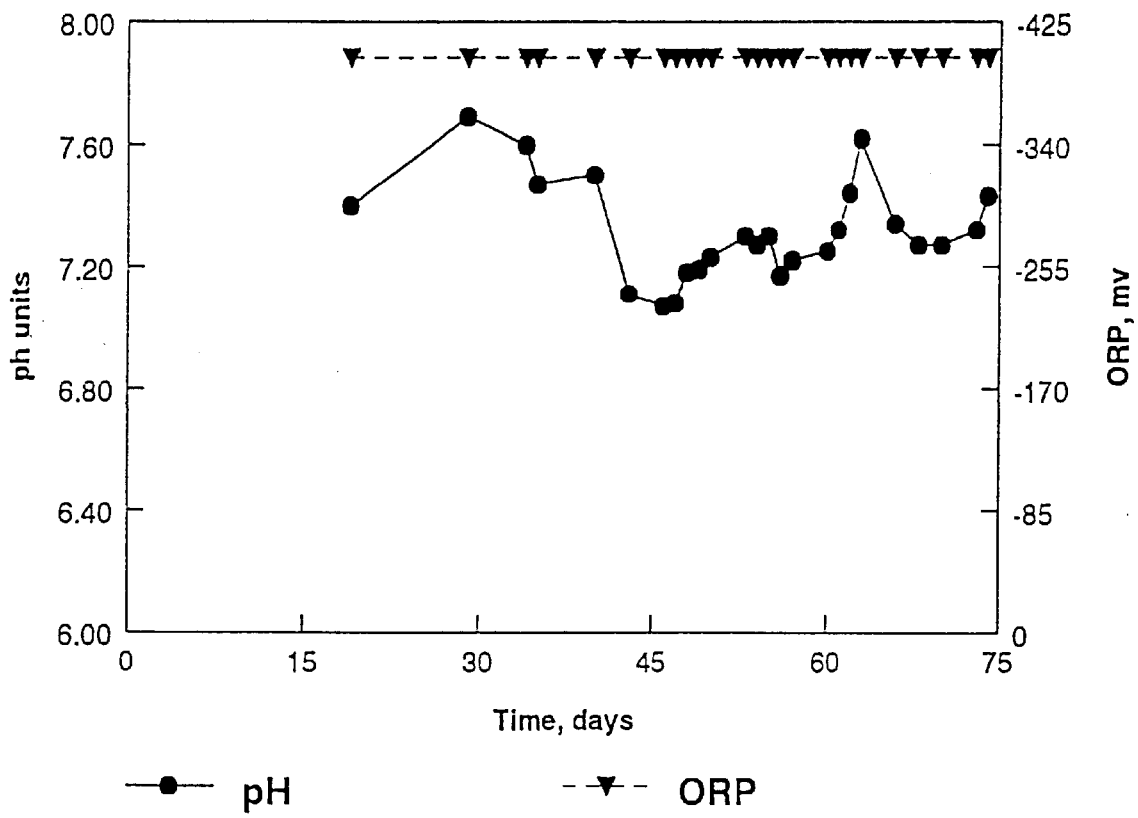
FIG. 10 is a graph representing the environmental conditions inside the methanogenesis biofilm reactor and illustrates the changes in pH and ORP.

Environmental conditions (i.e., pH, ORP) within the chemostats were monitored throughout the 74-day period. These conditions, mainly pH, also eluded to the fact that biodegradation was taking place. The environmental conditions inside the first denitrification reactor, the second denitrification reactor and the methanogenesis biofilm reactor are presented in FIGS. 8, 9 and 10, respectively. Increases in pH were attributed to biotransformation (production of basic acetate) and are noted in the figures as smooth-upswings in pH. Any downswings in pH were attributed to acid additions by the inventors in order to maintain a fairly constant pH value.

Total organic carbon samples were taken from the sample ports prior to the first denitrification reactor, following the second denitrification reactor and following the methanogenic reactor, and sent to an independent lab for analysis. Results of this analysis are presented in Table 9. The 10-ml samples were taken with a 10-ml gastight syringe and dispensed into a 10-ml serum bottle which was immediately capped with a Teflon® faced butyl rubber septum. The samples were purged for 12 minutes with nitrogen, prior to analysis on an ambient temperature oxidation total organic carbon analyzer.

Nitrate and nitrite concentrations were also monitored in the chemostats to supplement other data to confirm that biotransformation was occurring. Nitrate and nitrite analysis results are presented in Table 10. As biotransformation progressed in the chemostats, nitrate ($NO_3^-$) levels were reduced in each successive reactor (5 reactors), while nitrite ($NO_2^-$) levels increased.

TABLE 9

Independent Laboratory Total Organic Carbon Analysis (Day 74)

| Reactor | Port | Total organic carbon, mg/l (ppm) |
|---|---|---|
| Denitrification reactor #1 | Influent | 1830 |
| Denitrification reactor #1 | Effluent | 1700 |
| Denitrification reactor #2 | Effluent | 3000 |
| Methanogenesis biofilm reactor | Effluent | 1650 |
| Aerobic respiration | Effluent | 1700 |

TABLE 10

Change in Nitrate and Nitrite Concentrations During Biotransformation

| Day | Compound | Denitrif. chemostat 1 influent | Denitrif. chemostat 1 effluent | Denitrif. chemostat 2 effluent | Methanogenic reactor effluent | Aerobic reactor effluent |
|---|---|---|---|---|---|---|
| 7 | Nitrate | 637 | 549 | — | — | — |
|   | Nitrite | — | — | — | — | — |
| 10 | Nitrate | 669 | 519.2 | — | — | — |
|   | Nitrite | — | 11.13 | — | — | — |
| 11 | Nitrate | 693 | 504.2 | — | — | — |
|   | Nitrite | — | 6.29 | — | — | — |
| 12 | Nitrate | 668 | 533.8 | — | — | — |
|   | Nitrite | — | — | — | — | — |
| 13 | Nitrate | 696 | 538 | — | — | — |
|   | Nitrite | — | 5.8 | — | — | — |
| 27 | Nitrate | 546 | 490 | 333 | — | — |
|   | Nitrite | — | — | 34 | — | — |
| 28 | Nitrate | — | — | 300 | — | — |
|   | Nitrite | — | — | 80 | — | — |
| 31 | Nitrate | 539 | 461 | 414 | — | — |
|   | Nitrite | — | — | 40 | — | — |
| 32 | Nitrate | — | — | 316 | — | — |
|   | Nitrite | — | — | 66 | — | — |
| 33 | Nitrate | 512 | 483 | 345 | — | — |
|   | Nitrite | — | — | 35 | — | — |
| 45 | Nitrate | — | — | 127 | — | — |
|   | Nitrite | — | — | — | — | — |
| 53 | Nitrate | — | — | 123 | — | — |
|   | Nitrite | — | — | — | — | — |
| 76 | Nitrate | 143 | 134 | 122 | 0.15 | 50.3 |
|   | Nitrite | 0.09 | <0.05 | 0.10 | <0.05 | <0.05 |

During the analysis of the 27-day run of the prototype, the inventors experienced difficulties in raising the influent toxin concentrations up to the desired levels, (i.e., 100 mg/l for each BTEX compound, phenol, and cresols; and 1 mg/l for the chlorinated hydrocarbons). The flow of the toxins was increased to 0.5 microliters/min. at day 47 of the demonstration effort, due to preliminary results from the five previous days that showed the toxin levels were too low. By day 59, the influent concentrations of PCE, TCE and TCA were still too low. In order to remedy this problem, the influent concentrations of PCE, TCE and TCA were changed to 10,000 mg/l in the syringe pump at day 59. In addition, Viton tubing was substituted in the influent line. Toxin levels in the influent to the process increased to satisfactory levels, which were just below the desired influent concentrations.

Unfortunately, insufficient time was available for the reactors to completely reach steady state after the final adjustments were made. Table 11 presents the gas chromatograph results of the 20-day analysis performed in triplicate by the inventors.

As a supplement to the gas chromatography analysis by the inventors, splits were sent to an independent laboratory to have gas chromatography/mass spectrometry performed. The independent laboratory analyzed the samples by EPA Method 8260, which includes all of the constituents of the feed to the process, plus any toxic breakdown products that may have been produced. The inventors were interested in the breakdown products of the process to make sure toxic compounds (such as vinyl chloride) were not produced, as has been recorded in prior art. Surprisingly, only a small amount (0.069–0.088 mg/l) of methyl ethyl ketone (MEK) and 1,1 dichloroethane (0.035–0.045 mg/l) appeared in the effluent of the methanogenesis biofilm reactor. (The MEK may have leached from cements used in the fabrication of the reactors). Samples from day 74 were analyzed by only the independent laboratory. The results to the independent laboratory research are presented in Table 12.

Many variations in configurations have been discussed and others will occur to those skilled in the art. Some variations within the scope of the claims include industrial wastewater treatment and pump-and-treat and in-situ bioremediation implementations of the invention. All such variations within the scope of the claims are intended to be within the scope and spirit of the present invention.

TABLE 11

Average Influent and Effluent Concentrations - Inventor Measurements

| Constituent/day | Influent | Denitrification chemostat #1 effluent[a] | Denitrification chemostat #2 effluent[a] | Methanogenesis biofilm reactor effluent[a] | Aerobic respiration chemostat effluent |
|---|---|---|---|---|---|
| Benzene | | | | | |
| 48 | 10.0 | <0.1 | <0.1 | <0.1 | — |
| 52 | 21.5 | 23.7 | <0.1 | <0.1 | — |
| 56 | 24 | <0.1 | <0.1 | <0.1 | — |
| 59 | 20.4 | <0.1 | <0.1 | <0.1 | <0.1 |
| 63 | 67.90 | <0.1 | <0.1 | <0.1 | <0.1 |
| 67 | 53.6 | <0.1 | <0.1 | <0.1 | <0.1 |
| Toluene | | | | | |
| 48 | 1.4 | <0.1 | <0.1 | <0.1 | — |
| 52 | <0.1 | <0.1 | <0.1 | <0.1 | — |
| 56 | 4 | <0.1 | <0.1 | <0.1 | — |
| 59 | 110 | <0.1 | <0.1 | <0.1 | <0.1 |
| 63 | 29.13 | <0.1 | <0.1 | <0.1 | <0.1 |
| 67 | 28.9 | 7.70 | <0.1 | <0.1 | <0.1 |
| Ethylbenzene | | | | | |
| 48 | 2.0 | <0.1 | <0.1 | <0.1 | — |
| 52 | 5.4 | 3.0 | <0.1 | <0.1 | — |
| 56 | 10 | <0.1 | <0.1 | <0.1 | — |
| 59 | 9.9 | 0.97 | <0.1 | <0.1 | <0.1 |
| 63 | 23.0 | <0.1 | <0.1 | <0.1 | <0.1 |
| 67 | 21.3 | <0.1 | <0.1 | <0.1 | <0.1 |
| m + p-Xylenes | | | | | |
| 48 | 40 | 8.2 | 4.4 | — | — |
| 52 | 84.3 | 14.7 | 150 | 2.98 | — |
| 56 | 85 | 63 | 30 | 8.8 | — |
| 59 | 4.33 | 10 | 6.55 | 0.97 | <0.1 |
| 63 | 90.42 | 22.83 | 13.16 | 5.37 | <0.1 |
| 67 | 94.8 | 25.50 | 16.60 | 10.28 | <0.1 |
| o-Xylene | | | | | |
| 48 | 40 | 1.8 | 0.92 | — | — |
| 52 | 84.3 | 14.7 | 150 | 2.98 | — |
| 56 | 85 | 63 | 30 | 8.8 | — |
| 59 | 59 | 21.4 | 18.64 | 4.52 | <0.1 |
| 63 | 33.84 | 8.53 | 3.79 | 1.35 | <0.1 |
| 67 | 92.8 | 9.67 | 6.03 | 5.26 | <0.1 |
| Phenol | | | | | |
| 48 | — | — | — | — | — |
| 52 | 151 | 75 | —[b] | 4.0 | — |
| 56 | 416 | 56 | 41 | 8.5 | — |
| 59 | 105 | 38.6 | 20 | 6.84 | <0.1 |
| 63 | 129 | 29.85 | 35 | 7.65 | 7.50 |
| 67 | 199 | 142 | 27.9 | 19 | <0.1 |
| m-Cresol | | | | | |
| 48 | — | — | — | — | — |
| 52 | 88 | 36 | 33 | 2 | — |
| 56 | 71 | 59 | 49 | 10 | — |
| 59 | 46.6 | 21.0 | 12.9 | <0.1 | <0.1 |
| 63 | 84.8 | 26.2 | 10.76 | 3.86 | <0.1 |
| 67 | 111 | 21.0 | 8.1 | <0.1 | <0.1 |
| o-Cresol | | | | | |
| 48 | — | — | — | — | — |
| 52 | 125 | 38 | —[b] | 3 | — |
| 56 | 104 | 79 | 66 | 13.8 | — |
| 59 | 70.7 | 37.1 | 24.3 | 3.25 | <0.1 |
| 63 | 114 | 40.8 | 13.1 | 9.07 | <0.1 |
| 67 | 137 | 32 | 17.2 | 8.1 | <0.1 |
| p-Cresol | | | | | |
| 48 | — | — | — | — | — |
| 52 | 104 | <0.1 | —[b] | <0.1 | — |
| 56 | 93 | <0.1 | <0.1 | <0.1 | — |
| 59 | 59.2 | <0.1 | <0.1 | <0.1 | <0.1 |

TABLE 11-continued

Average Influent and Effluent Concentrations - Inventor Measurements

| | | Concentration, mg/l | | | |
|---|---|---|---|---|---|
| Constituent/ day | Influent | Denitrification chemostat #1 effluent[a] | Denitrification chemostat #2 effluent[a] | Methanogenesis biofilm reactor effluent[a] | Aerobic respiration chemostat effluent |
| 63 | 119.4 | <0.1 | <0.1 | <0.1 | <0.1 |
| 67 | 161 | <0.1 | <0.1 | #0.1 | <0.1 |
| PCE | | | | | |
| 48 | 0.002 | 0.002 | 0.005 | 0.02 | — |
| 52 | 0.06 | <0.001 | <0.001 | 0.02 | — |
| 56 | 0.11 | <0.001 | 0.003 | 0.018 | — |
| 59 | 0.11 | 0.001 | 0.004 | 0.015 | <0.001 |
| 63 | 4.27 | 0.011 | 0.0014 | 0.006 | <0.001 |
| 67 | 4.83 | 0.002 | 0.001 | 0.004 | <0.001 |
| TCE | | | | | |
| 48 | <0.001 | <0.001 | <0.001 | <0.001 | — |
| 52 | 0.04 | <0.001 | <0.001 | <0.001 | — |
| 56 | 0.43 | 0.002 | 0.01 | <0.001 | — |
| 59 | 0.44 | 0.009 | <0.001 | 0.035 | <0.001 |
| 63 | 4.79 | 0.19 | 0.24 | 0.19 | 0.031 |
| 67 | 5.26 | 0.340 | 0.002 | 0.126 | 0.229 |
| TCA | | | | | |
| 48 | 0.019 | 0.077 | 0.017 | 0.03 | — |
| 52 | 0.05 | 0.006 | <0.001 | 0.03 | — |
| 56 | 0.01 | 0.004 | 0.004 | 0.03 | — |
| 59 | 0.017 | 0.007 | <0.001 | 0.013 | <0.001 |
| 63 | 1.02 | 0.002 | 0.0013 | 0.0064 | <0.001 |
| 67 | 1.27 | 0.001 | <0.001 | 0.003 | 0.001 |

[a]Effluent from this reactor is influent into the next reactor.
[b]Represents outlying points.

TABLE 12

Independent Laboratory Confirmation of Average Influent and Effluent Concentrations

| | | Concentration, mg/l | | | |
|---|---|---|---|---|---|
| Constituent/ day | Influent | Denitrification chemostat #1 effluent[a] | Denitrification chemostat #2 effluent[a] | Methanogenesis biofilm reactor effluent[a] | Aerobic respiration chemostat effluent |
| Benzene | | | | | |
| 54 | 23.0 | 9.46 | 0.108 | 0.0023[d] | <0.01[b] |
| 59 | 17.0 | 10.4 | 0.103 | 0.0022[d] | <0.01[b] |
| 63 | 64.0 | 11.4 | 0.092 | 0.0012[d] | <0.01[b] |
| 67 | 76.2 | 18.4 | 0.113 | 0.0031[d] | 0.0016[d] |
| 74 | 22.8 | 27.3 | 0.134 | 0.0013[d] | <0.01[b] |
| Toluene | | | | | |
| 54 | 1.62 | 2.15 | 0.131 | 0.0073[d] | <0.01[b] |
| 59 | 4.49 | 1.96 | 0.162 | 0.010 | 0.0085[d] |
| 63 | 22.7 | 2.09 | 0.139 | 0.0039[d] | 0.0021[d] |
| 67 | 29.9 | 4.08 | 0.113 | 0.0099[d] | 0.0085[d] |
| 74 | 19.4 | 9.64 | 0.122 | 0.0058[d] | 0.0038[d] |
| Ethylbenzene | | | | | |
| 54 | 0.816 | 0.971 | 0.0056[d] | 0.0053[d] | <0.01[b] |
| 59 | 1.13 | 0.72 | 0.0065[d] | 0.0043[d] | 0.005[d] |
| 63 | 9.07 | 0.644 | 0.0068[d] | 0.0020[d] | 0.0015[d] |
| 67 | 13.3 | 1.27 | 0.0099[d] | 0.0068[d] | 0.0056[d] |
| 74 | 13.0 | 5.55 | <0.01[b] | <0.01[b] | <0.01[b] |
| m + p-Xylenes | | | | | |
| 54 | 1.50 | 1.99 | 0.020 | 0.022 | 0.0015[d] |
| 59 | 1.88 | 1.40 | 0.022 | 0.018 | 0.021 |
| 63 | 19.0 | 1.42 | 0.027 | 0.0085[d] | 0.0073[d] |

TABLE 12-continued

Independent Laboratory Confirmation of Average Influent and Effluent Concentrations

| | Concentration, mg/l | | | | |
|---|---|---|---|---|---|
| Constituent/ day | Influent | Denitrification chemostat #1 effluent[a] | Denitrification chemostat #2 effluent[a] | Methanogenesis biofilm reactor effluent[a] | Aerobic respiration chemostat effluent |
| 67 | 29.0 | 2.71 | 0.038 | 0.030 | 0.025 |
| 74 | 28.6 | 12.0 | 0.021 | 0.015[d] | <0.01[b] |
| o-Xylene | | | | | |
| 54 | 1.36 | 1.42 | 0.038 | 0.0078[d] | <0.01[b] |
| 59 | 1.60 | 1.07 | 0.036 | 0.0055[d] | 0.0062[d] |
| 63 | 12.20 | 1.07 | 0.037 | 0.0030[d] | 0.0022[d] |
| 67 | 17.2 | 1.88 | 0.043 | 0.0096[d] | 0.0079[d] |
| 74 | 16.8 | 7.57 | 0.038 | <0.01[b] | <0.01[b] |
| PCE | | | | | |
| 54 | <0.1 | <0.1[c] | <0.01[b] | 0.019 | <0.01[b] |
| 59 | <0.1[c] | <0.1[c] | <0.01[b] | 0.017 | <0.01[b] |
| 63 | 0.539 | <0.1[c] | 0.022 | 0.035 | 0.017 |
| 67 | 1.00 | 0.056[d] | <0.01[b] | 0.016 | <0.01[b] |
| 74 | 1.5 | .369 | <0.01[b] | 0.014 | <0.01[b] |
| TCE | | | | | |
| 54 | 0.034[d] | <0.1[c] | <0.01[b] | 0.012 | <0.01[b] |
| 59 | 0.096[d] | 0.014[d] | <0.01[b] | 0.0094[d] | <0.01[b] |
| 63 | 2.26 | 0.665[d] | <0.01[b] | 0.0088[d] | <0.01[b] |
| 67 | 3.60 | 0.379 | <0.01[b] | 0.0084[d] | <0.01[b] |
| 74 | 5.2 | 1.140 | <0.01[b] | <0.01[b] | <0.01[b] |
| 1,1-DCE | | | | | |
| 54 | <0.1[c] | <0.1[c] | <0.01[b] | <0.01[b] | <0.01[b] |
| 59 | <0.1[c] | <0.1[c] | <0.01[b] | <0.01[b] | <0.01[b] |
| 63 | <0.1[c] | <0.1[c] | <0.01[b] | <0.01[b] | <0.01[b] |
| 67 | <0.1[c] | <0.1[c] | <0.01[b] | <001[b] | <0.01[b] |
| 74 | <0.1[c] | <0.1[c] | <0.01[b] | <0.01[b] | <0.01[b] |
| cis-1,2-DCB | | | | | |
| 54 | <0.1[c] | <0.1[c] | <0.01[b] | <0.01[b] | <0.01[b] |
| 59 | <0.1[c] | <0.1[c] | <0.01[b] | <0.01[b] | <0.01[b] |
| 63 | <0.1[c] | <0.1[c] | <0.01[b] | <0.01[b] | <0.01[b] |
| 67 | <0.1[c] | <0.1[c] | <0.01[b] | <0.01[b] | <0.01[b] |
| 74 | <0.1[c] | <0.1[c] | <0.01[b] | <0.01[b] | <0.01[b] |
| trans-1,2-DCE | | | | | |
| 54 | <0.1[c] | <0.1[c] | <0.01[b] | <0.01[b] | <0.01[b] |
| 59 | <0.1[c] | <0.1[c] | <0.01[b] | <0.01[b] | <0.01[b] |
| 63 | <0.1[c] | <0.1[c] | <0.01[b] | <0.01[b] | <0.01[b] |
| 67 | <0.1[c] | <0.1[c] | <0.01[b] | <0.01[b] | <.001[b] |
| 74 | <0.1[c] | <0.1[c] | <0.01[b] | <0.01[b] | <0.01[b] |
| Vinyl chloride | | | | | |
| 54 | <0.1[c] | <0.1[c] | <0.01[b] | <0.01[b] | <0.01[b] |
| 59 | <0.1[c] | <0.1[c] | <0.01[b] | <0.01[b] | <0.01[b] |
| 63 | <0.1[c] | <0.1[c] | <0.01[b] | <0.01[b] | <0.01[b] |
| 67 | <0.1[c] | <0.1[c] | <0.01[b] | <0.01[b] | <0.01[b] |
| 74 | <0.1[c] | <0.1[c] | <0.01[b] | <0.01[b] | <0.01[b] |
| 1,1,1-TCA | | | | | |
| 54 | 0.138 | 0.049[d] | <0.01[b] | 0.0026[d] | <0.01[b] |
| 59 | 0.096[d] | 0.014[d] | <0.01[b] | 0.0094[d] | <0.01[b] |
| 63 | 2.26 | 0.065[d] | <0.01[b] | 0.0088[d] | <0.01[b] |
| 67 | 6.28 | 0.951 | 0.064 | 0.112 | 0.110 |
| 74 | 8.72 | 1.920 | <0.01[b] | <0.01[b] | <0.01[b] |
| 1,1-DCA | | | | | |
| 54 | <0.1[c] | <0.1[c] | <0.01[b] | 0.045 | <0.01[b] |
| 59 | <0.1[c] | <0.1[c] | <0.01[b] | 0.035 | <0.01[b] |
| 63 | <0.1[c] | <0.1[c] | <0.01[b] | 0.036 | <0.01[b] |
| 67 | <0.1[c] | <0.1[c] | <0.01[b] | <0.01[b] | <0.01[b] |
| 74 | <0.1[c] | <0.1[c] | <0.01[b] | 0.021 | <0.01[b] |
| 1,2-DCA | | | | | |
| 54 | <0.1[c] | <0.1[c] | <0.01[b] | <0.01[b] | <0.01[b] |
| 59 | <0.1[c] | <0.1[c] | <0.61[b] | <0.01[b] | <0.01[b] |
| 63 | <0.1[c] | <0.1[c] | <0.01[b] | <0.01[b] | <0.01[b] |

TABLE 12-continued

Independent Laboratory Confirmation of Average Influent and Effluent Concentrations

| | Concentration, mg/l | | | | |
|---|---|---|---|---|---|
| Constituent/ day | Influent | Denitrification chemostat #1 effluent[a] | Denitrification chemostat #2 effluent[a] | Methanogenesis biofilm reactor effluent[a] | Aerobic respiration chemostat effluent |
| 67 | <0.1[c] | <0.1[c] | <0.01[b] | <0.01[b] | <0.01[b] |
| 74 | <0.1[c] | <0.1[c] | <0.01[b] | <0.01[b] | <0.01[b] |
| Chloroethane | | | | | |
| 54 | <0.1[c] | <0.1[c] | <0.01[b] | <0.01[b] | <0.01[b] |
| 59 | <0.1[c] | <0.1[c] | <0.01[b] | <0.01[b] | <0.01[b] |
| 63 | <0.1[c] | <0.1[c] | <0.01[b] | <0.01[b] | <0.01[b] |
| 67 | <0.1[c] | <0.1[c] | <0.01[b] | <0.01[b] | <0.01[b] |
| 74 | <0.1[c] | <0.1[c] | <0.01[b] | <0.01[b] | <0.01[b] |

[a]Effluent from this reactor is influent to the next reactor.
[b]Compound was not detected at this (undiluted) detection limit.
[c]Compound was not detected at this (diluted 100 to 1) detection limit.
[d]Estimated value - was detected at a level that was below the normal detection limit

We claim:

1. A process for biodegradation of benzene comprising cultivating a microorganism (ATTC 55712 or a mutant thereof) in an aqueous medium comprising benzene and dissolved nitrate, under anaerobic conditions.

2. An axenic culture of the microorganism having the ATTC accession number 55712, or a mutant thereof.

3. A freeze-dried culture of the microorganism having the ATCC accession number 55712, or a mutant thereof.

4. A pure culture of a microorganism, ATCC 55712, or a mutant thereof, said culture being capable of metabolizing benezene.

5. A mixed culture of microorganisms comprising:
a plurality of microorganisms ATCC 55712 or a mutant thereof, said plurality comprising at least 90 percent of the microorganisms in said mixed culture;
wherein said mixed culture is capable of degrading benzene in a denitrification reaction.

6. An enrichment culture having the identifying characteristics of ATCC 55712.

7. A culture comprising the microorganism ATCC 55712 or a mutant thereof, said culture being capable of degrading benzene under essentially anaerobic conditions.

* * * * *